United States Patent
Yamamoto et al.

[11] Patent Number: 5,932,233
[45] Date of Patent: Aug. 3, 1999

[54] COSMETIC COMPOSITIONS

[75] Inventors: Tomoyuki Yamamoto; Yumiko Sato; Seiji Yamasaki; Atsushi Nakajima; Masataka Fukuda, all of Tokyo, Japan

[73] Assignee: Kao Corporation, Tokyo, Japan

[21] Appl. No.: 08/949,961

[22] Filed: Oct. 14, 1997

[30] Foreign Application Priority Data

Nov. 7, 1996 [JP] Japan .................................. 8-295033

[51] Int. Cl.⁶ ...................................................... A61K 7/48
[52] U.S. Cl. ........................ 424/401; 514/625; 514/627; 514/629; 514/844
[58] Field of Search ............................ 424/401; 514/844, 514/625, 627, 629

[56] References Cited

U.S. PATENT DOCUMENTS 5,476,671  12/1995  Cho et al. .............................. 424/70.1

FOREIGN PATENT DOCUMENTS

| 0 487 958 | 6/1992 | European Pat. Off. . |
| 0 691 327 | 1/1996 | European Pat. Off. . |
| WO 94/23694 | 10/1994 | WIPO . |
| WO 96/37462 | 11/1996 | WIPO . |

OTHER PUBLICATIONS

Patent Abstracts of Japan vol. 095, No. 003, of JP 06 345633 A, Dec. 20, 1994.

*Primary Examiner*—Jyothsna Venkat
*Attorney, Agent, or Firm*—Oblon, Spivak, McClelland, Maier & Neustadt, P.C.

[57] ABSTRACT

Described is a cosmetic composition comprising (A) an amide compound having a melting point of 0 to 50° C. and (B) a hydrophilic surfactant. The cosmetic composition according to the present invention can enhance the water-retaining ability of the stratum corneum and is excellent in skin-roughness lessening effects.

5 Claims, No Drawings

COSMETIC COMPOSITIONS

BACKGROUND OF THE INVENTION

1. Field of the Invention

The present invention relates to cosmetic compositions which can enhance water-retaining ability of the stratum corneum of the skin and are excellent in skin-roughness lessening effects.

2. Description of the Related Art

Skin troubles such as rough skin, dry skin and aged skin are considered to occur because of the lowering in the water content of the stratum corneum. It is known that amide-bond-containing compounds, for example, intercellular lipids, particularly sphingolipid, are effective for overcoming such troubles. There has been an attempt to incorporate such compound in a cosmetic composition in order to heighten the water-retaining ability of the stratum corneum, thereby lessening or preventing skin roughness.

It is however difficult to stably incorporate the amide-bond-containing compound in a cosmetic composition or the like and therefore, sufficient skin-roughness lessening effects have not been attained so far.

SUMMARY OF THE INVENTION

An object of the present invention is therefore to provide a cosmetic composition which can enhance water-retaining ability of the stratum corneum and therefore has excellent skin-roughness lessening effects.

With the forgoing in view, the present inventors have carried out an extensive investigation. As a result, it has been found that the use of a specific amide compound and a hydrophilic surfactant in combination makes it possible to provide a cosmetic composition in which an amide compound has been incorporated stably, can enhance water-retaining ability of the stratum corneum and is excellent in the skin-roughness lessening effects, leading to the completion of the invention.

In the present invention, there is thus provided a cosmetic composition comprising the following components (A) and (B):

(A) an amide compound having a melting point ranging from 0° C. to 50° C.; and (B) a hydrophilic surfactant.

DETAILED DESCRIPTION OF THE PREFERRED EMBODIMENTS

The amide compound usable as the component (A) in the present invention has a melting point ranging from 0 to 50° C., preferably 10 to 40° C. The amide compounds having the melting point outside the above range cannot be incorporated in the composition stably.

In the present invention, incidentally, the melting point was indicated by extrapolation melt starting point as measured in accordance with JIS-K-7121-1987-9-9.1(2).

Examples of such an amide compound include acid amides such as isostearic acid amide, isopalmitic acid amide and isomyristic acid amide, an acylglutamic acid phytostearyl ester and amide derivatives represented by the following formulas (1) to (3):

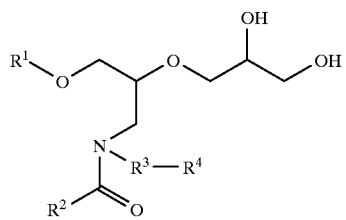

wherein $R^1$ and $R^2$ are the same or different and each independently represents a $C_{1-40}$ hydrocarbon group which may be hydroxylated, $R^3$ represents a linear or branched $C_{1-6}$ alkylene group or a single bond, $R^4$ represents a hydrogen atom, a linear or branched $C_{1-12}$ alkoxy group or a 2,3-dihydroxypropyloxy group, with the proviso that when $R^3$ represents a single bond, $R^4$ is a hydrogen atom.

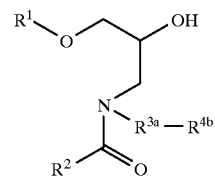

wherein $R^1$ and $R^2$ have the same meanings as defined above, $R^{3a}$ represents a linear or branched $C_{3-6}$ alkylene group, $R^{4a}$ represents a linear or branched $C_{1-12}$ alkoxy group.

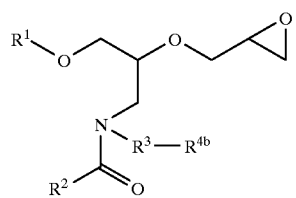

wherein $R^1$, $R^2$ and $R^3$ have the same meanings as defined above, $R^{4b}$ represents a hydrogen atom, a linear or branched $C_{1-12}$ alkoxy group or a 2,3-epoxypropyloxy group, with the proviso that when $R^3$ represents a single bond, $R^{4b}$ is a hydrogen atom.

In the amide derivative (1), among these amide derivatives, $R^1$ and $R^2$ are the same or different and each independently represents a linear or branched, saturated or unsaturated $C_{1-40}$ hydrocarbon group which may be hydroxylated. Examples of $R^1$ and $R^2$ include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, heneicosyl, docosyl, nonacosyl, triacontyl, isostearyl, isoheptadecyl, 2-ethylhexyl, 1-ethylheptyl, 8-heptadecyl, 8-heptadecenyl, 8,11-heptadecadienyl, 2-heptylundecyl, 9-octadecenyl, 1-hydroxynonyl, 1-hydroxypentadecyl, 2-hydroxypentadecyl, 15-hydroxypentadecyl, 11-hydroxyheptadecyl and 11-hydroxy-8-heptadecenyl.

As $R^1$, linear or branched $C_{8-26}$ alkyl or alkenyl groups are preferred and specific examples include octyl, decyl, dodecyl, tetradecyl, hexadecyl, octadecyl, docosyl, triacontyl, isostearyl, 2-ethylhexyl, 2-heptylundecyl and 9-octadecenyl. Particularly preferred hydrocarbon groups as $R^1$ are linear or branched $C_{12-22}$ alkyl groups such as dodecyl, tetradecyl, hexadecyl, octadecyl, docosyl and methyl-branched isostearyl.

As $R^2$, linear or branched $C_{9-25}$ alkyl or alkenyl groups are preferred. Specific examples include nonyl, undecyl, tridecyl, pentadecyl, heptadecyl, heneicosyl, nonacosyl, isoheptadecyl, 1-ethylheptyl, 8-heptadecyl, 8-heptadecenyl, 8,11-heptadecadienyl, 1-hydroxynonyl, 1-hydroxypentadecyl, 2-hydroxypentadecyl, 15-hydroxypentadecyl, 11-hydroxyheptadecyl and 11-hydroxy-8-heptadecenyl groups. Particularly preferred hydrocarbon groups as $R^2$ are linear or branched $C_{11-21}$ alkyl groups such as undecyl, tridecyl, pentadecyl, heptadecyl, heneicosyl and methyl-branched isoheptadecyl groups.

$R^3$ represents a linear or branched $C_{1-6}$ alkylene group or a single bond. Illustrative alkylene groups include methylene, ethylene, trimethylene, tetramethylene, pentamethylene, hexamethylene, 1-methylethylene, 1-methyltrimethylene, 2-methyltrimethylene, 1,1-dimethylethylene, 1-ethylethylene, 1-methyltetramethylene, 2-ethyltrimethylene groups. As $R^3$, linear $C_{1-6}$ alkylene groups are preferred, with methylene, ethylene and trimethylene being particularly preferred.

$R^4$ represents a hydrogen atom, a linear or branched $C_{1-12}$ alkoxy group or a 2,3-dihydroxypropyloxy group. Illustrative alkoxy groups include methoxy, ethoxy, propoxy, butoxy, hexyloxy, octyloxy, decyloxy, 1-methylethoxy and 2-ethylhexyloxy groups. As $R^4$, preferred are a hydrogen atom, Cl-a alkoxy groups and a 2,3-dihydroxypropyloxy group, with a hydrogen atom, and methoxy, ethoxy, propoxy, butoxy, 1-methylethoxy, 2-ethylhexyloxy and 2,3-dihydroxypropyloxy groups being particularly preferred.

As an amide derivative (1), particularly preferred are compounds having the formula (1) in which $R^1$, $R^2$, $R^3$ and $R^4$ are those selected in combination from the above-described particularly preferred ranges.

In the amide derivative (2), $R^1$ and $R^2$ have the same meanings as described above and the same groups are preferably used. Examples of $R^{3a}$ are similar to the alkylene groups exemplified as $R^3$ in the amide derivative (1) except for the omission of methylene and ethylene. As $R^{3a}$, linear $C_{3-6}$ alkylene groups are preferred, with trimethylene being particularly preferred. Examples of $R^{4a}$ are similar to the alkoxy groups as exemplified as $R^4$ in the amide derivative (1). Preferred examples are also similar to those of $R^4$ in (1).

In the amide derivative (3), $R^1$, $R^2$ and $R^3$ have the same meanings as defined above. $R^{4b}$ represents a hydrogen atom, a linear or branched $C_{1-12}$ alkoxy group or a 2,3-epoxypropyloxy group. Specific examples of $R^1$, $R^2$ and $R^3$ are similar to those exemplified above with respect to the amide derivative (1). Their preferred examples are similar to those mentioned above. Examples of the linear or branched $C_{1-12}$ alkoxy group as $R^{4b}$ are similar to those of $R^4$ in the amide derivative (1). Specifically, a hydrogen atom, alkoxy groups similar to those exemplified above as $R^4$ and a 2,3-epoxypropyloxy group are preferred.

Among the amide derivatives (1) to (3), those represented by the formula (1) are particularly preferred.

The amide derivative (1) can be obtained, for example, by the following Preparation Process 1 or Preparation Process 2.

Preparation Process 1

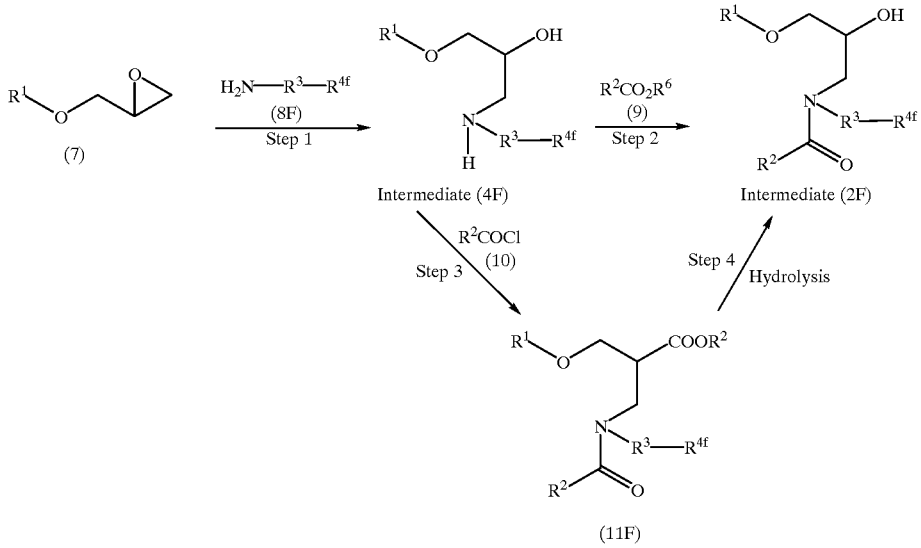

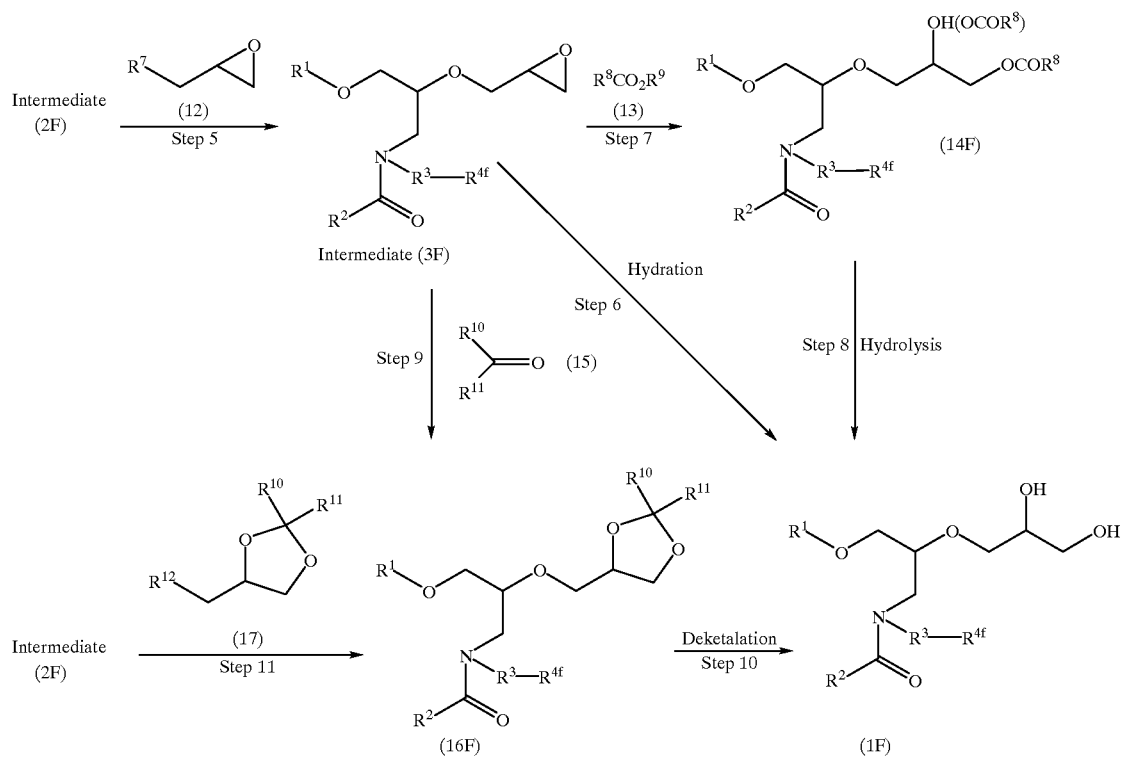

wherein $R^1$, $R^2$ and $R^3$ have the same meanings as defined above and $R^{4f}$ represents a hydrogen atom or a linear or branched $C_{1-12}$ alkoxy group, with the proviso that $R^{4f}$ is a hydrogen atom when $R^3$ represents a signal bond. $R^6$, $R^8$, $R^{10}$ and $R^{11}$ individually represent a linear or branched, saturated or unsaturated $C_{1-8}$ hydrocarbon group, with a linear or branched $C_{1-5}$ alkyl group being preferred and with a methyl group being particularly preferred. $R^9$ represents a hydrogen atom, an alkali metal atom or a $COR^8$ group, and $R^7$ and $R^{12}$ individually represent an eliminative atom or group such as halogen atom, mesylate group or tosylate group. From the standpoint of availability and the like, $R^7$ is preferably a chlorine atom or bromine atom, with a chlorine atom being particularly preferred. From the standpoint of availability and the like, $R^{12}$ is preferably a mesylate group or tosylate group.

Preparation Process 2

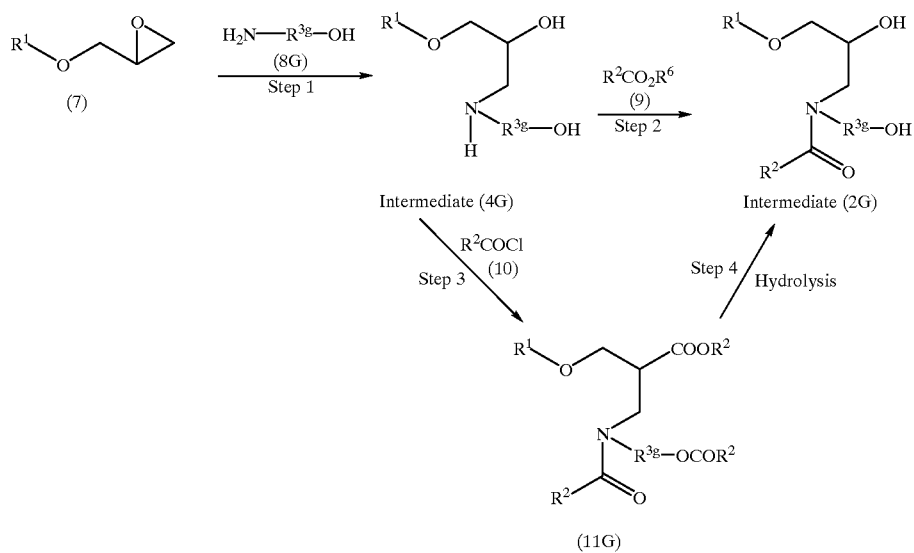

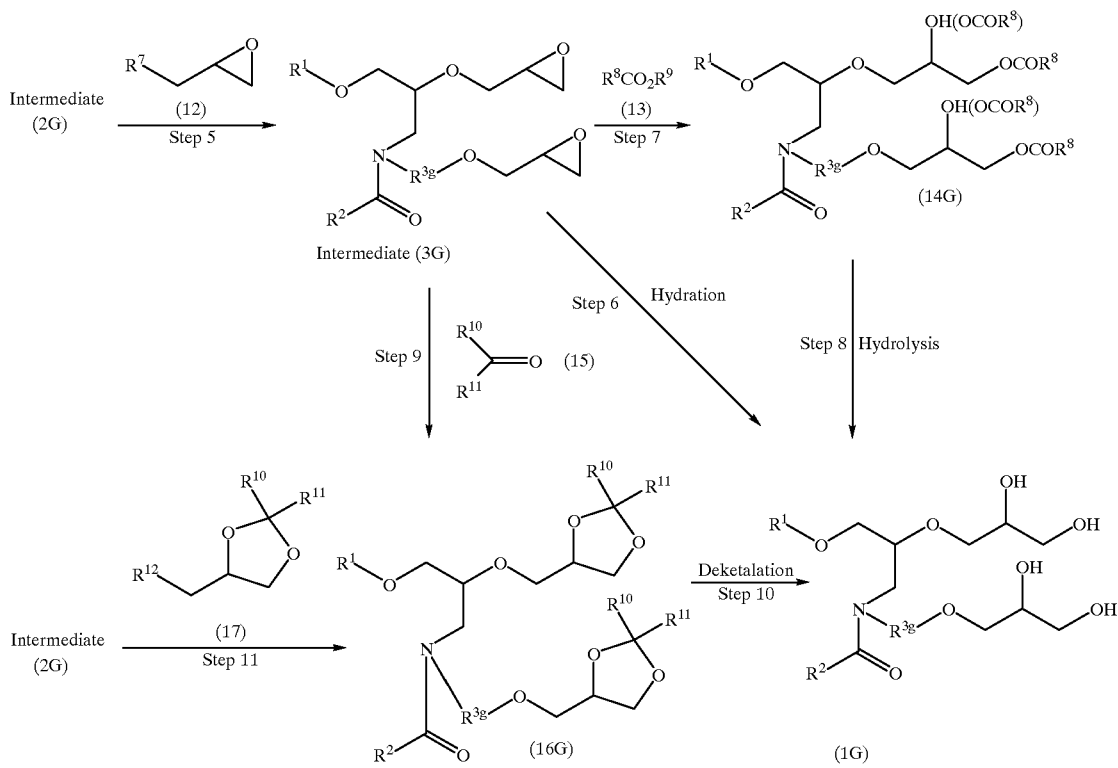

wherein $R^1$, $R^2$, $R^6$ to $R^{12}$ have the same meanings as defined above, and $R^{3g}$ represents a linear or branched alkylene group having 1 to 6 carbon atoms.

Reaction conditions for the individual steps of the Preparation Process 1 and Preparation Process 2 are as follows:

Step 1)

An amino alcohol derivative (4F) or (4G) can be prepared by reacting a glycidyl ether (7) and an amine (8F) or (8G) at room temperature to 150° C. either in a solventless manner or in the presence of water, a lower alcohol such as methanol, ethanol or isopropanol, an ether solvent such as tetrahydrofuran, dioxane or ethylene glycol dimethyl ether, a hydrocarbon solvent such as hexane, benzene, toluene or xylene, or a mixed solvent of desired two or more solvents thereof.

Step 2)

An amide derivative (2F) or (2G) can be prepared by reacting the amino alcohol derivative (4F) or (4G) with a fatty acid ester (9), preferably a lower alkyl ester of a fatty acid such as the methyl ester of a fatty acid or the ethyl ester of a fatty acid under a reduced pressure of from normal pressure to 0.01 mmHg at room temperature to 150° C. in the presence of a basic catalyst, for example, an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, or an alkali metal alcoholate such as sodium methoxide, sodium ethoxide or potassium tert-butoxide. Here, the basic catalyst may be used preferably in an amount of 0.01 to 0.2 equivalent based on the amino alcohol derivative (4F) or (4G). It is preferred to conduct the reaction while taking the resulting alcohol out of the system, as the reaction is allowed to proceed at a higher velocity.

Step 3)

The amide derivative (2F) or (2G) can also be prepared by reacting the amino alcohol derivative (4F) or (4G) with a fatty acid chloride (10) at room temperature to 100° C. either in a solventless manner or in a halogenated hydrocarbon solvent such as chloroform, methylene chloride or 1,2-dichloroethane, an ether solvent such as tetrahydrofuran, dioxane or ethylene glycol dimethyl ether, a hydrocarbon solvent such as hexane, benzene, toluene or xylene or in a mixed solvent of desired two or more solvents thereof in the presence or absence of a base, for example, a tertiary amine such as pyridine or triethylamine to convert the amino alcohol derivative (4F) or (4G) into an amide ester derivative (11F) or (11G) and then, Step 4)

by selectively hydrolyzing its ester group under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal alcoholate such as sodium methoxide, sodium ethoxide or potassium tert-butoxide.

Step 5)

An amide derivative (3F) or (3G) can be prepared by reacting, at room temperature to 150° C., the amide derivative (2F) or (2G) with 1 to 20 equivalents of an epoxide (12), preferably epichlorohydrin either in a solventless manner or in water, an ether solvent such as tetrahydrofuran, dioxane or ethylene glycol dimethyl ether, a hydrocarbon solvent such as hexane, benzene, toluene or xylene or a mixed solvent of desired two or more solvents thereof in the presence of 1 to 10 equivalents of an alkali metal hydroxide such as potassium hydroxide or sodium hydroxide, an alkaline earth metal hydroxide such as calcium hydroxide, an alkali metal carbonate such as potassium carbonate or an alkaline earth metal carbonate such as calcium carbonate. From the standpoint of its yield and the like, it is preferred to conduct the reaction in the presence of a phase transfer catalyst, for example, a quaternary ammonium salt such as tetrabutylammonium bromide, tetrabutylammonium chloride, hexadecyltrimethylammonium chloride, hexadecyltrimethylammonium bromide, stearyltrimethylammonium chloride or bis-tetraoxyethylene stearylmethylammonium chloride, or a betaine such as lauryldimethylcarboxyammonium betaine.

Step 6)

An amide derivative (1F) or (1G) can be prepared by hydrating the amide derivative (3F) or (3G) at room temperature to 300° C. under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate or an alkaline earth metal carbonate such as calcium carbonate, under acidic conditions, for example, in the presence of a mineral acid such as sulfuric acid or hydrochloric acid, a Lewis acid such as boron trifluoride or tin tetrachloride, a carboxylic acid such as acetic acid, tetradecanoic acid or hexadecanoic acid or a sulfonic acid such as p-toluenesulfonic acid, or under mixed base-acid conditions.

Step 7)

The amide derivative (1F) or (1G) can also be prepared by reacting the amide derivative (3F) or (3G) with one or more carboxylic acid derivatives (13), preferably lower fatty acids such as acetic acid, alkali metal salts of lower fatty acids such as sodium acetate, lower fatty acid anhydrides such as acetic anhydride either singly or in combination in the presence or absence of a basic catalyst, for example, a tertiary amine such as triethylamine to convert the amide derivative (3F) or (3G) into an ester-amide derivative (14F) or (14G) and then, Step 8)

by selecting hydrolyzing its ester group under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal alcoholate such as sodium methoxide, sodium ethoxide or potassium tert-butoxide.

Step 9)

The amide derivative (1F) or (1G) can also be prepared by reacting the amide derivative (3F) or (3G) with a carbonyl compound (15), preferably a lower fatty acid ketone such as acetone or methyl ethyl ketone in the presence of an acid catalyst, for example, a mineral acid such as sulfuric acid, hydrochloric acid or phosphoric acid, a carboxylic acid such as acetic acid, or Lewis acid such as boron trifluoride or tin tetrachloride to convert the amide derivative (3F) or (3G) into a 1,3-dioxolane-amide derivative (16F) or (16G) and then, Step 10)

by subjecting the 1,3-dioxolane-amide derivative (16F) or (16G) to deketalation under acidic conditions, for example, in the presence of a mineral acid such as sulfuric acid, hydrochloric acid or phosphoric acid, a carboxylic acid such as acetic acid or a sulfonic acid such as p-toluenesulfonic acid.

Step 11)

The 1,3-dioxolane-amide derivative (16F) or (16G) can also be prepared by reacting the amide derivative (2F) or (2G) with a glycerol derivative (17) in the presence of a base, for example, an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal hydride such as sodium hydride either in a solventless manner or in an aprotic polar solvent such as N,N-dimethylformamide or dimethylsulfoxide, an ether solvent such as tetrahydrofuran, dioxane or ethylene glycol dimethyl ether, a hydrocarbon solvent such as hexane, benzene, toluene or xylene, or a mixed solvent of desired two or more solvents thereof.

The amide derivative (1) which has been obtained as described above can be purified by a method known per se in the art. In the present invention, the amide derivative (1) can be used either in the form of a compound purified to 100% purity or in the form of a mixture of a purity of 70% or higher but lower than 100% containing one or more intermediates and/or one or more reaction by-products while assuring excellent effects and performance without safety problem. It is to be noted that the amide derivative (1) include its solvates typified by it hydrate.

Examples of the amide derivative (1) which can be obtained following the Preparation Process 1 include the following compounds:

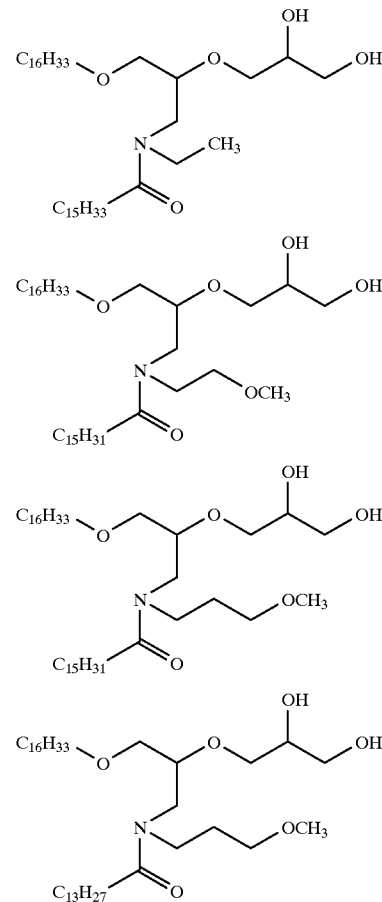

-continued

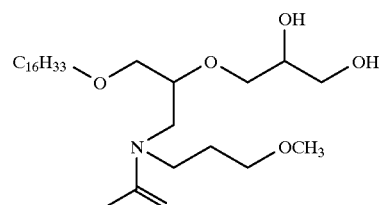

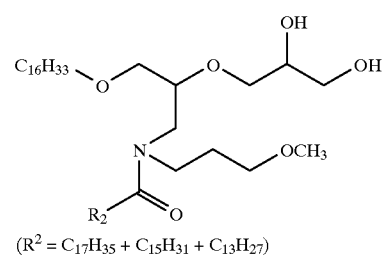

(R² = C₁₇H₃₅ + C₁₅H₃₁ + C₁₃H₂₇)

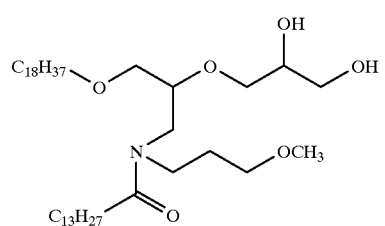

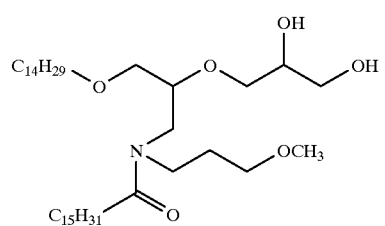

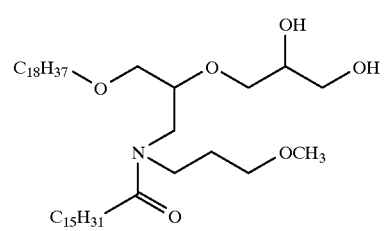

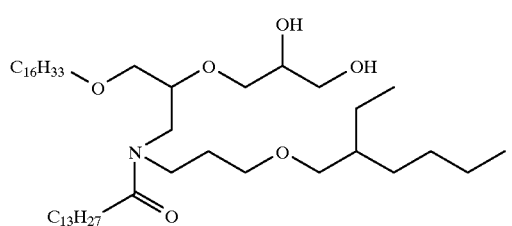

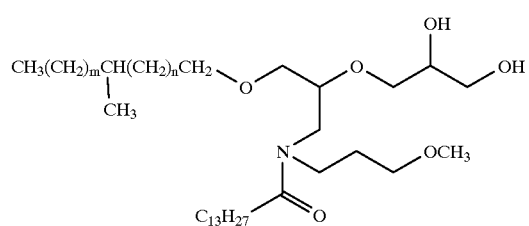

wherein m and n represents numerals having distributions centered at m = 7 and n = 7 with m + n in a range of from 10 to 16, m in a range of from 4 to 10 and n in a range of from 4 to 10.

-continued

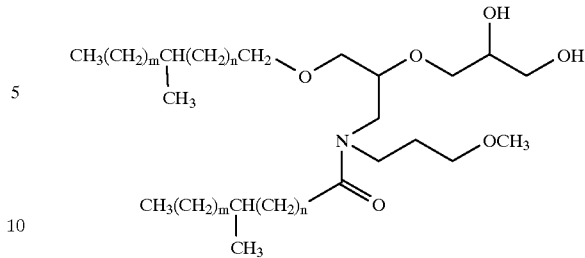

wherein m and n have the same meanings as defined above.

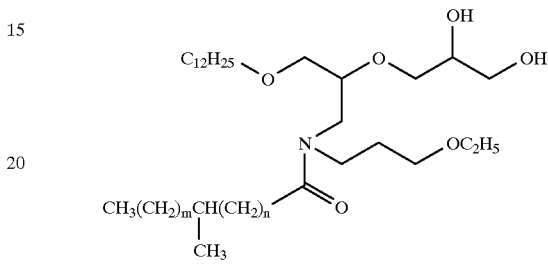

wherein m and n have the same meanings as defined above.

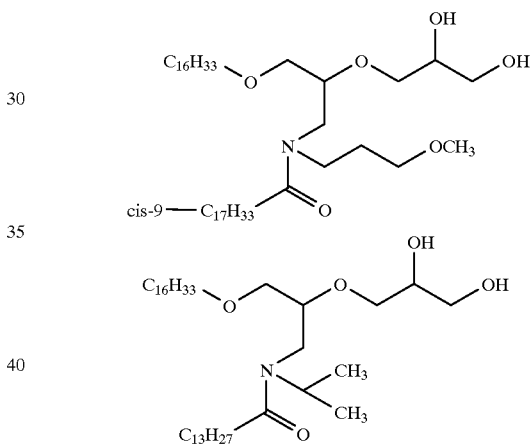

Examples of the amide derivative (1) which can be obtained following the Preparation Process 2 include the following compounds:

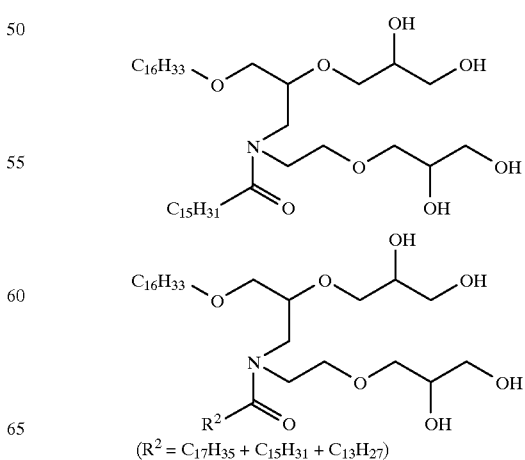

(R² = C₁₇H₃₅ + C₁₅H₃₁ + C₁₃H₂₇)

-continued

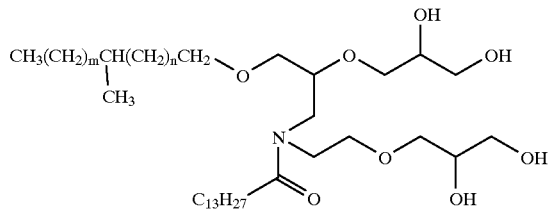

wherein m and n represent numerals having distributions centered at m=7 and n=7 with m+n in a range of from 10 to 16, m in a range of from 4 to 10 and n in a range of from 4 to 10.

As the amide compound as Component (A), N-substituted amide compounds having at least 30 carbon atoms in total are particularly preferred.

Besides, as the amide compound, those capable of retaining bound water in an amount of 1 wt. % or greater, particularly 5 wt. % or greater are preferred. Here, the content of bound water can be determined by adding water to the sample at room temperature, measuring as the amount of bound water the maximum amount of water that can be added until a uniform phase is lost, and finding the percentage of the total amount of the bound water to the total amount of the sample in accordance with the following formula:

$$\frac{\text{Total amount of water (g)}}{\text{Total amount of the sample (g)}} \times 100 = \text{bound water content (wt. \%)}$$

The amide compounds as Component (A) can be used either singly or in combination. The amide compound is preferably added in an amount of 0.02 to 20 wt. % based on the whole composition, with 0.02 to 10 wt. % being particularly preferred. From the viewpoint of stability, the addition in an amount of 0.02 to 5 wt. % is more preferred.

As a hydrophilic surfactant usable in the present invention as Component (B), no particular limitation is imposed on it insofar as it can be used conventionally for cosmetic compositions. Any one of nonionic surfactant, anionic surfactant, amphoteric surfactant and cationic surfactant can be used. The term "hydrophilic surfactant" as used herein means a surfactant having compatibility with water.

Specific examples of the nonionic surfactant include polyoxyethylene-added surfactants, for example, polyoxyethylene castor oils and derivatives of hydrogenated castor oils such as polyoxyethylene castor oil and polyoxyethylene hydrogenated castor oil, polyoxyethylene sorbitan fatty acid esters such as polyoxyethylene sorbitan monostearate and polyoxyethylene sorbitan tetraoleate, fatty acid esters of polyoxyethylene glycol such as polyoxyethylene glyceryl monoisostearate and polyoxyethylene glyceryl trisostearate, and polyoxyethylene alkyl ethers such as polyoxyethylene octyl dodecyl ether, polyoxyethylene lauryl ether, polyoxyethylene cetyl ether, polyoxyethylene stearyl ether and polyoxyethylene nonyl phenyl ether; polyglycerin alkyl ethers; polyglycerin fatty acid esters; and sucrose fatty acid esters.

Examples of the anionic surfactant include polyoxyethylene alkyl sulfates such as polyoxyethylene lauryl ether sodium sulfate and polyoxyethylene lauryl ether triethanolamine sulfate; N-acylamino acid salts such as lauroyl sarcosine sodium and lauroyl methylalanine sodium; polyoxyethylene alkyl ether phosphates such as polyoxyethylene lauryl ether sodium phosphate, polyoxyethylene cetyl ether sodium phosphate, dipolyoxyethylene alkyl ether phosphoric acid, tripolyoxyethylene alkyl ether phosphoric acid, dipolyoxyethylene nonylphenyl ether phosphoric acid, polyoxyethylene lauryl ether sodium phosphate and dipolyoxyethylene lauryl ether sodium phosphate. Among them, polyoxyethylene alkyl ether sodium phosphate is particularly preferred.

Illustrative amphoteric surfactants include alkylbetaine and alkylamidobetaine.

Exemplary cationic surfactants include di(long chain) alkyl quaternary ammonium salts, mono(long chain)alkyl quaternary ammonium salts, di(long chain)alkyl polyoxyethylene quaternary ammonium salts, bis(hydroxyalkyl) quaternary ammonium salts and quaternary ammonium salts containing an amide/ether bond.

Among the above exemplified surfactants, nonionic surfactants, particularly polyoxyethylene hydrogenated castor oil, polyoxyethylene alkyl ether and polyoxyethylene sorbitan are preferred, with those having an HLB of 8 to 20, particularly those having an HLB of 10 to 16 being more preferred.

The above-exemplified surfactants as Component (B) can be used either singly or in combination. It is preferred to add it in an amount of 0.0002 to 10 wt. % based on the whole composition, with 0.0002 to 5 wt. %, particularly 0.0002 to 3 wt. % being more preferred from the viewpoint of the stability.

The weight ratio of Component (A) to Component (B) is preferably 1:0.01 to 1:10, particularly 1:0.4 to 1:5 from the viewpoint of stability.

To the cosmetic composition of the present invention, it is possible to add, besides the above-described ingredients, other ingredients used for conventional cosmetic compositions, for example, water-soluble alcohols such as ethanol, glycerin, sorbitol, propylene glycol, dipropylene glycol or 1,3-butanediol, water-soluble high molecules, acids, bases, salts, perfumes, colorants, antioxidants, ultraviolet absorbers, whitening agents, blood-circulation accelerators, vitamins, sequestering agents, lipid controllers, powders, astringents, skin softeners, surfactants other than those described above, lubricants and water. They can be used as needed within an extent not impairing the advantages of the present invention. Here, water can be incorporated in the cosmetic composition of the present invention in an amount of 70 to 99.9 wt. %.

The cosmetic composition of the present invention can be prepared in the conventional manner. It can be formulated into various forms, for example, cosmetic skin care formulations such as water/oil or oil/water emulsion cosmetic compositions, creams, cosmetic emulsions, toilet waters, oil-base cosmetics, lipsticks, foundations, and skin-cleansing formulations.

Clear or semi-clear cosmetic compositions can be obtained by selecting the components as needed.

The cosmetic compositions according to the present invention stably contain an amide compound having good miscibility or mixing stability so that it can enhance water-retaining ability of the stratum corneum and has excellent effects for lessening or preventing skin roughness.

EXAMPLES

The present invention will hereinafter be described on the basis of the following examples. It is however to be borne in mind that the present invention is not limited to or by the following examples. In Preparation Example 1 to 10, the amide derivatives (1) were prepared following the Preparation Process 1.

Preparation Example 1

In a 2-liter five-necked flask fitted with a stirrer, a dropping funnel, a nitrogen inlet tube and a distillation equipment, 743.2 g (8.34 mol) of 3-methoxypropylamine and 150 ml of ethanol were charged and, while the resulting mixture was stirred under heat at 80° C. under a nitrogen atmosphere, 165.9 g (0.56 mol) of hexadecyl glycidyl ether were added dropwise to the mixture over 3 hours. After completion of the dropwise addition, the reaction mixture was stirred at 80° C. for 12 hours and the ethanol and excess 3-methoxypropylamine were distilled out under heat and reduced pressure. The residue was purified by chromatography on a silica gel column, whereby 196.5 g of an aminoalcohol derivative (4a) were obtained (yield: 91% based on the hexadecyl glycidyl ether) (step 1).

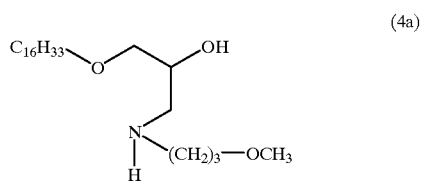

(4a)

The followings are physical properties of the amino alcohol derivative (4a) so obtained.

White solid.
Melting point: 53° C.
IR($\nu_{near}$, cm$^{-1}$) 3340, 2930, 2855, 1470, 1310, 1120, 1065, 955, 900, 720.
$^1$H-NMR(CDCl$_3$, δ): 0.88(t,J=6.3Hz,3H), 1.25–1.45(m, 26H), 1.45–1.85(m,6H), 2.57–2.76(m,4H), 3.32(s,3H), 3.38–3.48(m,6H), 3.77–3.89(m,1H).

In a 1-liter five-necked flask fitted with a stirrer, a dropping funnel, a nitrogen inlet tube and a distillation equipment, 61.3 g (158.1 mmol) of the compound (4a), which had been obtained above (step 1) and had been molten, and 1.53 g (7.91 mmol) of a 28% methanol solution of sodium methoxide were charged, followed by stirring at 60° C. for 30 minutes under a nitrogen atmosphere. Under the same conditions, 38.3 g (158.1 mmol) of methyl tetradecanoate were added dropwise to the resultant mixture over 1 hour. After completion of the dropwise addition, the reaction mixture was stirred at 60° C. for 5 hours under reduced pressure (80–10 Torr) so that the reaction was brought to completion. The reaction mixture was cooled and then purified by chromatography on a silica gel column, whereby 88.7 g of an amide derivative (2a) were obtained (yield: 94%) (step 2).

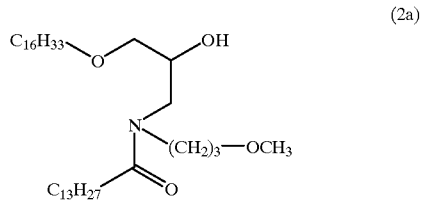

(2a)

The followings are physical properties of the amide derivative (2a) so obtained.

White solid.
Melting point: 48° C.
IR($\nu_{near}$, cm$^{-1}$): 3440, 2930, 2860, 1650, 1625, 1470, 1225, 1210, 1110, 950, 720.
$^1$H-NMR(CDCl$_3$, δ): 0.88(br t,J=6.3Hz,6H), 1.15–1.95 (m,53H), 2.36(t,J=7.5Hz,2H), 3.29–3.55(m,10H), 3.33(s,3H), 3.85–3.95(m,1H).

In a 1-liter five-necked flask fitted with a stirrer, a nitrogen inlet tube and a distillation equipment, 94.5 g (158.0 mmol) of the compound (2a) obtained above (step 2), 1.53 g (4.74 mmol) of tetrabutylammonium bromide, 32.2 g (347.6 mmol) of epichlorohydrin, 12.6 g (315.0 mmol) of sodium hydroxide and 66 ml of toluene were charged, followed by stirring at 45° C. for 10 hours under a nitrogen atmosphere. After the reaction mixture so obtained was washed three times at 70° C. with water, the toluene and excess epichlorohydrin were distilled out under heat and reduced pressure and the residue was purified by chromatography on a silica gel column, whereby 94.9 g of an amide derivative (3a) were obtained (yield: 92%) (step 5).

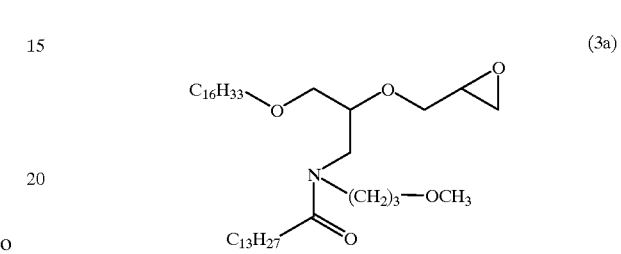

(3a)

The followings are physical properties of the amide derivative (3a) so obtained.

White solid.
Melting point: 38–39° C.
IR($\nu_{near}$, cm$^{-1}$): 2930, 2855, 1650, 1470, 1425, 1380, 1210, 1120, 905, 840, 720.
$^1$H-NMR(CDCl$_3$, δ): 0.88(br t,J=6.0Hz,6H), 1.10–1.45 (m,46H), 1.45–1.90(m,6H), 2.25–2.48(m,2H), 2.50–2.68(m, 1H), 2.70–2.85(m,1H), 3.02–3.20(m,1H), 3.20–4.00(m, 13H), 3.32(s,3H).

Into a 100-ml autoclave fitted with a stirrer, 71.3 g (109.0 mmol) of the compound obtained above (step 5), 11.78 g (654.1 mmol) of water, 0.087 g (2.18 mmol) of sodium hydroxide and 0.87 g (4.36 mmol) of tetradecanoic acid were charged, followed by stirring at 160° C. for 6 hours in a closed system. After the reaction mixture was cooled, it was washed twice at 80° C. with a 2% aqueous solution of NaCl and then purified by chromatography on a silica gel column, whereby 68.3 of a target amide derivative (1a) were obtained (yield: 93%) (step 6).

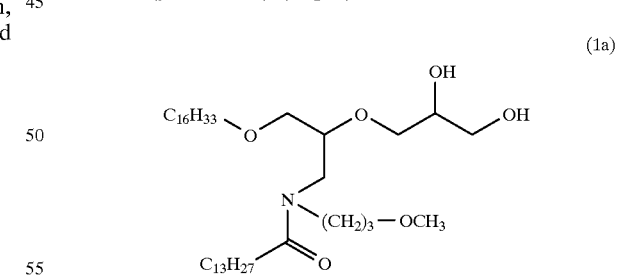

(1a)

The followings are physical properties of the amide derivative (1a) so obtained.

Colorless clear liquid.
IR($\nu_{near}$, cm$^{-1}$) 3445, 2930, 2860, 1630, 1470, 1420, 1380, 1305, 1210, 1120, 720.
$^1$H-NMR (CDCl$_3$, δ): 0.88(br t,J=6.7Hz,6H), 1.15–1.44 (m,46H), 1.44–1.95(m,8H), 2.25–2.45(m,2H), 3.20–3.90(m, 16H), 3.33(s,3H).

Into a 500-ml four-necked flask fitted with a stirrer, a nitrogen inlet tube and a distillation equipment, 31.0 g (47.7 mmol) of the compound (3a) obtained above (step 5), 11.9 g (663.7 mmol) of water, 13.6 g (165.9 mmol) of sodium acetate and 104.9 g (1746.8 mmol) of acetic acid were charged, followed by stirring at 70° C. for 19 hours under a nitrogen atmosphere. Excess acetic acid was distilled out under heat and reduced pressure, whereby a mixture containing ester-amide derivatives (14a-1), (14a-2) and (14a-3) were obtained (step 7).

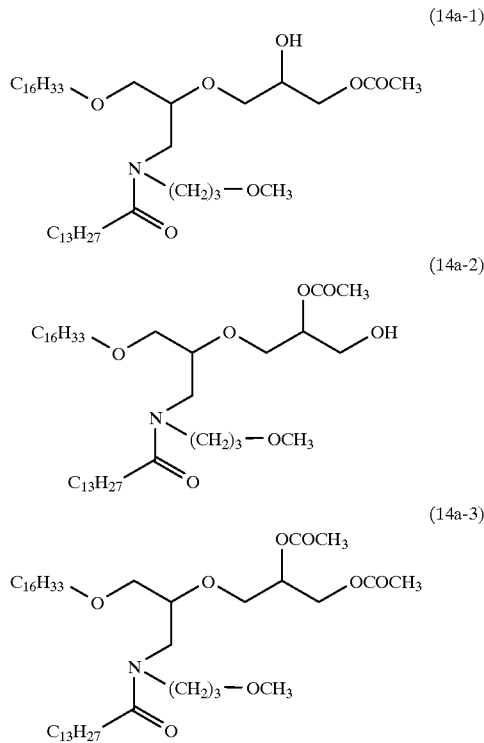

The mixture containing those ester-amide derivatives, without being taken out of the flask, were next added with 59.3 g (711.2 mmol) of a 48% aqueous solution of sodium hydroxide, 18 g of water and 200 ml of butanol, followed by stirring at 80° C. for 3 hours. The butanol was distilled out under heat and reduced pressure. After the residue was diluted in 250 ml of toluene, the resultant solution was washed twice at 70° C. with water. The toluene was distilled out under heat and reduced pressure and the residue was purified by chromatography on a silica gel column, whereby 22.3 g of the intended amide derivative (1a) were obtained (yield: 70%) (step 8).

Preparation Example 2

Into a 10-liter five-necked flask fitted with a stirrer, a dropping funnel, a nitrogen inlet tube and a distillation equipment, 4680 g (52.5 mol) of 3-methoxypropylamine and 900 g of ethanol were charged and, while the resulting mixture was stirred at 80° C. under heat and a nitrogen atmosphere, 1045 g (3.50 mol) of hexadecyl glycidyl ether were added dropwise to the mixture over 3 hours. After completion of the dropwise addition, the reaction mixture was stirred at 80° C. for 1 hour and the ethanol and excess 3-methoxypropylamine were distilled out under heat and reduced pressure, whereby a product composed of an amino alcohol derivative (4a) as a principal component was obtained (step 1).

To the product obtained above (step 1), which was composed of the compound (4a) as the principal component and was contained in the 10-liter five-necked flask, 9.82 g (0.175 mol) of potassium hydroxide were added. Under ebullation of nitrogen, the resultant mixture was stirred under reduced pressure (60 to 100 Torr) at 80° C. for 3 hours while distilling out the resulting water. With stirring under the same conditions, 882.3 g (3.64 mol) of methyl tetradecanoate were next added dropwise to the reaction mixture over 3 hours. During the dropwise addition, the resulting methanol was distilled out. After completion of the dropwise addition, the mixture was stirred under ebullation of nitrogen and reduced pressure (60 to 10 Torr) at 60 to 45° C. for 10 hours while distilling out the resulting methanol, whereby the reaction was brought to completion and a compound composed of an amide derivative (2a) as a principal component was obtained (step 2).

To the product obtained above (step 2), composed of the compound (2a) as the principal component and contained in the 10-liter five-necked flask, 33.9 g (0.105 mol) of tetrabutylammonium bromide, 712.5 g (7.70 mol) of epichlorohydrin and 2100 g of toluene were added. Under ebullition of nitrogen, 1750.0 g (21.0 mol) of a 48% aqueous solution of sodium hydroxide were added dropwise under reduced pressure (150 to 50 Torr) at 45° C. with stirring over 2 hours. After completion of the dropwise addition, the resultant mixture was stirred for 10 hours under the same conditions to bring the reaction to completion. After the reaction mixture was washed four times at 70° C. with water, the toluene and excess epichlorohydrin were distilled out under heat and reduced pressure, whereby a product composed of an amide derivative (3a) as a principal component was obtained (step 5).

To the product obtained above (step 5), composed of the compound (3a) as the principal component and contained in the 10-liter five-necked flask, 378.2 g (21.0 mol) of water, 5.83 g (0.070 mol) of a 48% aqueous solution of sodium hydroxide and 32.0 g (0.14 mol) of tetradecanoic acid were added, followed by stirring at 100° C. for 2.5 days under a nitrogen atmosphere. After the reaction mixture was washed three times at 80° C. with a 2% aqueous solution of NaCl, water was eliminated under heat and reduced pressure, whereby 2261.5 g of a product composed of a target compound (1a) as a principal component were obtained (step 6). The product contained the compound (1a) in an amount of 70% and in addition, also contained intermediates, reaction byproducts and the like represented by the following formulae:

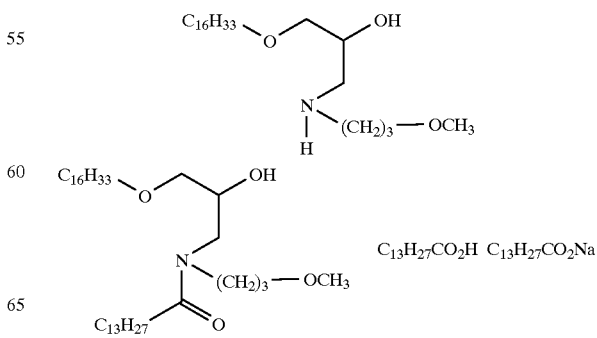

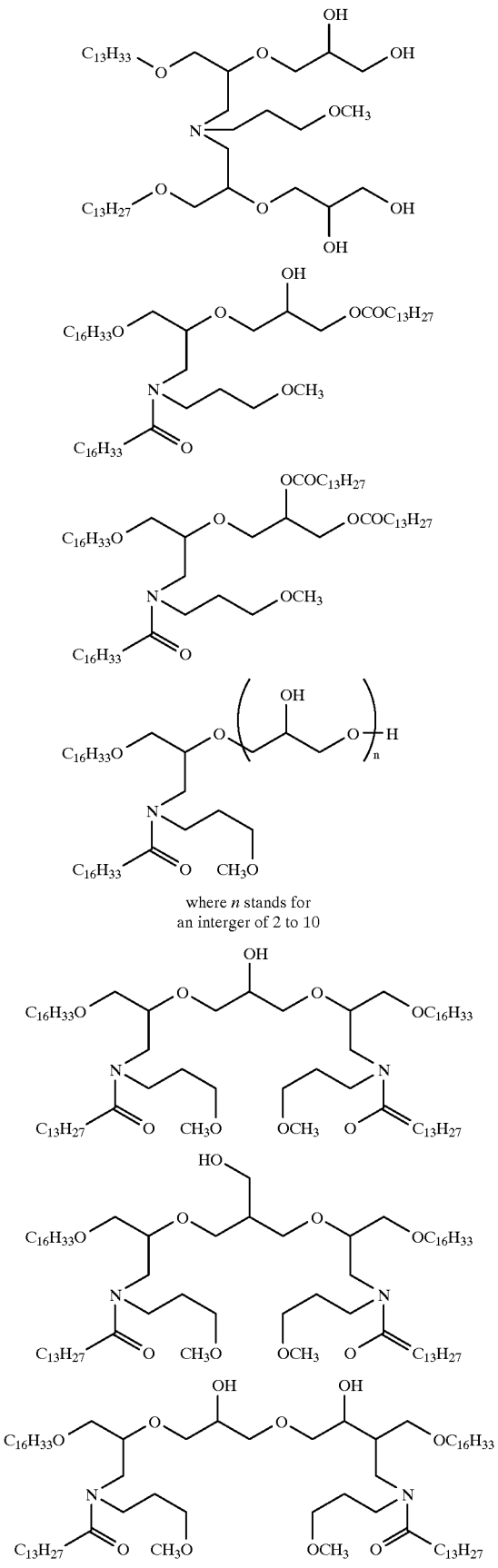

where $n$ stands for an interger of 2 to 10

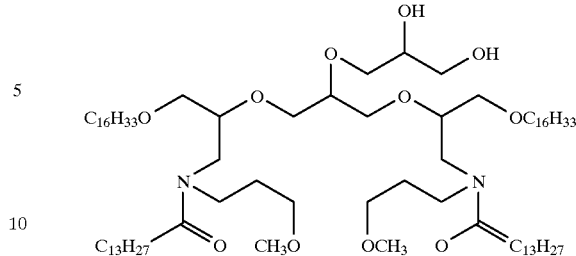

Preparation Example 3

An amide derivative (2b) was obtained by conducting reactions as in steps 1 and 2 of Preparation Example 1 except that in step 2 of Preparation Example 1, methyl hexadecanoate was used in lieu of methyl tetradecanoate (steps 1 and 2).

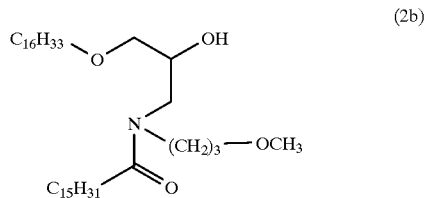

(2b)

The followings are physical properties of the amide derivative (2b) so obtained.

White solid.

Melting point: 55° C.

IR($\nu_{neat}$, cm$^{-1}$): 3430, 2930, 2855, 1620, 1470, 1205, 1110, 950, 720.

$^1$H-NMR(CDCl$_3$, $\delta$): 0.88(br t,J=6.4Hz,6H), 1.26–1.89 (m,57H), 2.36(t,J=7.6Hz, 2H), 3.29–3.52(m,10H), 3.33(s, 3H), 3.88–3.95(m,1H).

An amide derivative (3b) was obtained by conducting a reaction as in step 5 of Preparation Example 1 except that in step 5 of Preparation Example 1, the compound (2b) obtained above (step 2) was used in lieu of the compound (2a) (step 5).

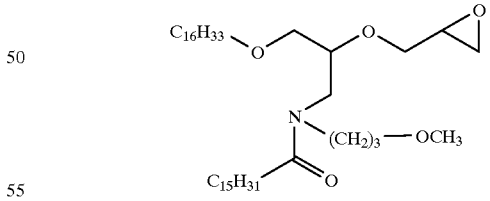

(3b)

The followings are physical properties of the amide derivative (3b) so obtained.

White solid.

Melting point: 44–45° C.

IR($\nu_{neat}$, cm$^{-1}$): 2930, 2860, 1650, 1470, 1425, 1380, 1210, 1120, 910, 845, 755, 720.

$^1$H-NMR(CDCl$_3$, $\delta$): 0.88(br t,J=6.7Hz,6H), 1.15–1.45 (m,50H), 1.45–1.73(m,4H), 1.73–1.90(m,2H), 2.25–2.48(m, 2H), 2.50–2.68(m,1H), 2.70–2.85(m,1H), 3.00–3.18(m,1H), 3.18–4.00(m,13H), 3.32(s,3H).

A target amide derivative (1b) was obtained by conducting a reaction as in step 6 of Preparation Example 1 except that in step 6 of Preparation Example 1, the compound (3b) obtained above (step 5) was used in lieu of the compound (3a) and hexadecanoic acid was employed in place of tetradecanoic acid (step 6).

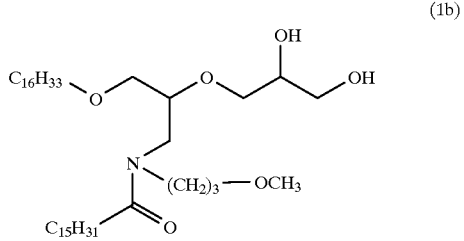
(1b)

The followings are physical properties of the amide derivative (1b) so obtained.

White solid.

Melting point: 33° C.

IR($\nu_{neat}$, cm$^{-1}$): 3445, 2930, 2860, 1650, 1630, 1470, 1420, 1380, 1305, 1210, 1120, 1080.

$^1$H-NMR(CDCl$_3$, δ): 0.88(br t,J=6.4Hz,6H), 1.15–1.45 (m,50H), 1.45–1.95(m,7H), 2.25–2.55(m,3H), 3.20–3.92(m, 16H), 3.33(s,3H).

Into a 500-ml four-necked flask fitted with a stirrer and a nitrogen inlet tube, 34.1 g (50.0 mmol) of the compound (3b) obtained above (step 5), 25.5 g (250.0 mmol) of acetic anhydride and 25.3 g (250.0 mmol) of triethylamine were charged, followed by stirring at 100° C. for 10 hours under a nitrogen atmosphere. The reaction mixture was concentrated under heat and reduced pressure and the residue so obtained was purified by chromatography on a silica gel column, whereby 34.9 g of an ester-amide derivative (14b) were obtained (yield: 89%) (step 7).

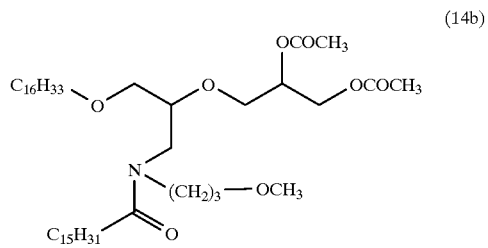
(14b)

The followings are physical properties of the ester-amide derivative (14b) so obtained.

Brown clear liquid.

$^1$H-NMR(CDCl$_3$, δ): 0.88(br t,J=6.4Hz,6H), 1.26–1.83 (m,56H), 2.03–2.20(m,6H), 2.33(t,J-7.1Hs,2H), 3.12–4.35 (m,15H), 3.32(s,3H), 5.04–5.43(m,1H).

Into a 200-ml four-necked flask fitted with a stirrer and a nitrogen inlet tube, 33.9 g (43.2 mmol) of the compound (14b) obtained above (step 7), 0.42 g (2.16 mmol) of a 28% methanol solution of sodium methoxide and 200 ml of methanol were charged, followed by stirring at room temperature for 3.5 hours under a nitrogen atmosphere. The reaction mixture was concentrated under heat and reduced pressure and the residue so obtained was purified by chromatography on a silica gel column, whereby 16.0 g of a target amide derivative (1b) were obtained (yield: 53%) (step 8).

Into a 3-liter four-necked flask fitted with a stirrer and a nitrogen inlet tube, 45.2 g (72.0 mmol) of the compound (2b) obtained above (step 2), 2.86 g (119.2 mmol) of sodium hydride and 800 ml of toluene were charged, followed by stirring at 55° C. for 30 minutes under a nitrogen atmosphere. Next, 34.8 g (121.5 mmol) of 1,2-isopropylidenedioxy-3-tosyloxypropane were added to the resultant mixture, followed by stirring at 100° C. for 18 hours. The reaction mixture was added under ice cooling with 20 ml of 2-propanol to inactivate unreacted sodium hydride and was then concentrated under heat and reduced pressure. The residue so obtained was purified by chromatography on a silica gel column, whereby 51.0 g of a 1,3-dioxolane-amide derivative (16b) were obtained (yield: 96%) (step 11).

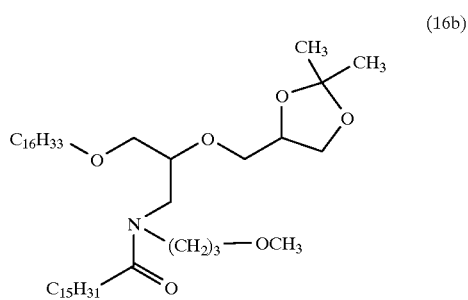
(16b)

The followings are physical properties of the 1,3-dioxolane-amide derivative (16b) so obtained.

Colorless clear liquid.

$^1$H-NMR(CDCl$_3$, δ): 0.88(br t,J=6.4Hz,6H), 1.20–1.90 (m,62H), 2.36(t,J-7.0Hz,2H), 3.30–4.25(m,19H).

Into a 2-liter four-necked flask fitted with a stirrer and a nitrogen inlet tube, 51.0 g (68.9 mmol) of the compound (16b) obtained above (step 11), 0.50 g (2.63 mmol) of tosyl acid monohydrate and 500 ml of methanol were charged, followed by stirring at room temperature for 12 hours under a nitrogen atmosphere. The reaction mixture was concentrated under heat and reduced pressure and the residue so obtained was purified by chromatography on a silica gel column, whereby 41.0 g of a target amide derivative (1b) was obtained (yield: 85%) (step 10).

Preparation Example 4

An amide derivative (2c) was obtained by conducting reactions as in step 1 and step 2 of Preparation Example 1 except that in step 2 of Preparation Example 1, methyl dodecanoate was used instead of methyl tetradecanoate (steps 1 and 2).

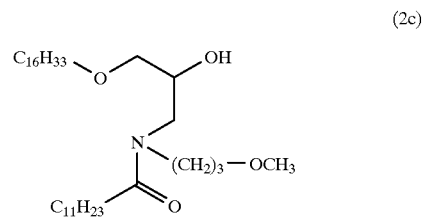
(2c)

The followings are physical properties of the amide derivative (2c) so obtained.

Colorless clear liquid.

IR($\nu_{neat}$, cm$^{-1}$): 3435, 2930, 2855, 1620, 1470, 1220, 1110, 720.

¹H-NMR(CDCl₃, δ): 0.88(br t,J=6.4Hz,6H), 1.20–1.90 (m,49H), 2.36(t,J=7.6Hz,2H), 3.25–3.52(m,10H), 3.33(s, 3H), 3.88–3.95(m,1H).

An amide derivative (3c) was obtained by conducting a reaction as in step 5 of Preparation Example 1 except that in step 5 of Preparation Example 1, the compound (2c) obtained above (step 2) was used in lieu of the compound (2a) (step 5).

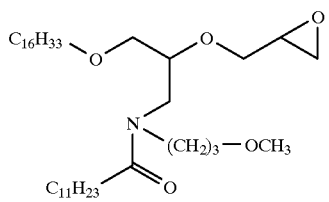

(3c)

The followings are physical properties of the amide derivative (3c) so obtained.

Pale yellow liquid.

IR($v_{near}$, cm⁻¹): 2940, 2875, 1750, 1650, 1470, 1380, 1210, 1120, 910, 845.

¹H-NMR (CDCl₃, δ) 0.88(br t,J=6.4Hz,6H), 1.15–1.45 (m,42H), 1.45–1.75(m,4H), 1.75–1.90(m,2H), 2.25–2.50(m, 2H), 2.50–2.68(m,1H), 2.70–2.85(m,1H), 3.00–3.18(m,1H), 3.18–4.00(m,13H), 3.32 (s, 3H).

A target amide derivative (1c) was obtained by conducting reactions as in step 7 and step 8 of Preparation Example 1 except that in step 7 of Preparation Example 1, the compound (3c) obtained above (step 5) was used instead of the compound (3a) (steps 7 and 8).

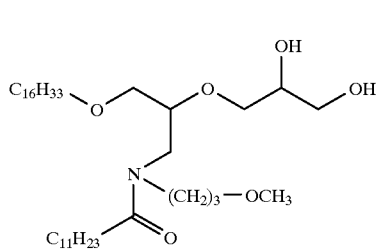

(1c)

The followings are physical properties of the amide derivative (1c) so obtained.

Colorless clear liquid.

IR($v_{near}$, cm⁻¹) 3430, 2930, 2860, 1650, 1630, 1470, 1380, 1260, 1210, 1115, 1080, 795, 720.

¹H-NMR(CDCl₃, δ): 0.88(br t,J=6.7Hz,6H), 1.15–1.45 (m,42H), 1.45–1.97(m,8H), 2.25–2.45(m,2H), 3.15–3.92(m, 16H), 3.33(s,3H).

Preparation Example 5

An amide derivative (2d) was obtained by conducting reactions as in step 1 and step 2 of Preparation Example 1 except that in step 2 of Preparation Example 1, the methyl ester of "Lunac P-70" (trade name for a 3:70:27 mixture by weight ratio of tetradecanoic acid, hexadecanoic acid and octadecanoic acid; product of Kao Corporation), said methyl ester having been prepared by reacting "Lunac P-70" with methanol in the presence of sulfuric acid as a catalyst under heat and reflux, was used in place of methyl tetradecanoate (steps 1 and 2).

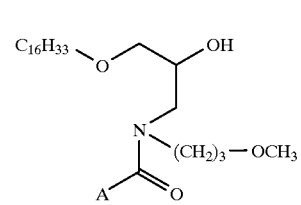

(2d)

wherein A represents a mixture of $C_{13}H_{27}$, $C_{15}H_{31}$ and $C_{17}H_{35}$.

The followings are physical properties of the amide derivative (2d) so obtained.

White solid.

Melting point: 50° C.

IR($v_{near}$, cm⁻¹): 3430, 2930, 2860, 1620, 1470, 1205, 1110, 950, 720.

A target amide derivative (1d) was obtained by conducting reactions as in step 11 and step 10 of Preparation Example 3 except that in step 11 of Preparation Example 3, the reaction was conducted using the compound (2d), which had been obtained above (step 2), instead of the compound (2b) and in the next step 10, the reaction was conducted without purification of the thus-obtained 1,3-dioxolane-amide derivative (16d) (steps 11 and 10).

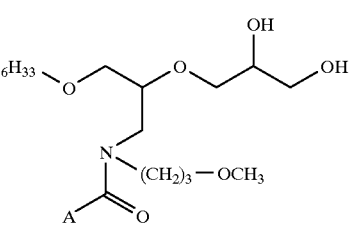

(1d)

wherein A represents a mixture of $C_{13}H_{27}$, $C_{15}H_{31}$ and $C_{17}H_{35}$.

The followings are physical properties of the amide derivative (1d) so obtained.

White solid.

Melting point: 32° C.

IR($v_{near}$, cm⁻¹): 3445, 2930, 2860, 1650, 1630, 1470, 1380, 1210, 1120, 1080, 720.

Preparation Example 6

An amino alcohol derivative (4e) was obtained by conducting a reaction as in step 1 of Preparation Example 1 except that in step 1 of Preparation Example 1, octadecyl glycidyl ether was used instead of hexadecyl glycidyl ether (step 1).

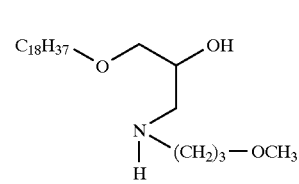

(4e)

The followings are physical properties of the amino alcohol derivative (4e) so obtained.

White solid.

Melting point: 57–58° C.

IR($v_{near}$, cm$^{-1}$): 3340, 2930, 2855, 1470, 1120, 960, 900, 840, 720.

$^1$H-NMR(CDCl$_3$, δ): 0.88(br t,J=6.3Hz,3H), 1.25–1.45 (m,30H), 1.45–1.85(m,6H), 2.55–2.75(m,4H), 3.32(s,3H), 3.35–3.50(m,6H), 3.77–3.89(m,1H).

An amide derivative (2e) was obtained by conducting a reaction as in step 2 of Preparation Example 1 except that in step 2 of Preparation Example 1, the compound (4e) obtained above (step 1) was used in lieu of the compound (4a) (step 2).

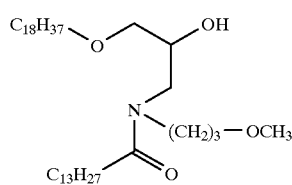
(2e)

The followings are physical properties of the amide derivative (2e) so obtained.

White solid.

Melting point: 49° C.

IR($v_{near}$, cm$^{-1}$): 3440, 2930, 2860, 1650, 1625, 1470, 1225, 1210, 1110, 950, 720.

$^1$H-NMR (CDCl$_3$, δ): 0.88(br t,J=6.3Hz,6H), 1.15–1.95 (m,57H), 2.36(t,J=7.5Hz, 2H), 3.30–3.55(m,10H), 3.33(s, 3H), 3.85–3.95(m,1H).

An amide derivative (3e) was obtained by conducting a reaction as in step 5 of Preparation Example 1 except that in step 5 of Preparation Example 1, the compound (2e) obtained above (step 2) was used instead of the compound (2a) (step 5).

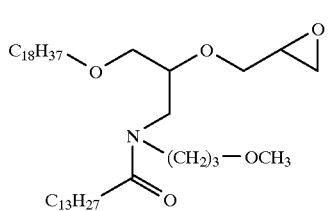
(3e)

The followings are physical properties of the amide derivative (3e) so obtained.

Colorless clear liquid.

IR($v_{near}$, cm$^{-1}$) 2930, 2860, 1650, 1425, 1380, 1260, 1210, 1120, 910, 720.

$^1$H-NMR(CDCl$_3$, δ): 0.88(br t,J=6.0Hz,6H), 1.10–1.45 (m,50H), 1.45–1.90(m,6H), 2.25–2.50(m,2H), 2.50–2.68(m, 1H), 2.70–2.85(m,1H), 3.01–3.20(m,1H), 3.20–4.00(m, 13H), 3.32(s,3H).

A target amide derivative (1e) was obtained by conducting reactions as in steps 7 and 8 of Preparation Example 1 except that in step 7 of Preparation Example 1, the compound (3e) obtained above (step 5) was used instead of the compound (3a) (steps 7 and 8).

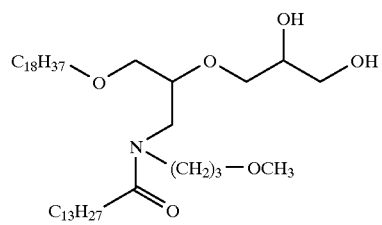
(1e)

The followings are physical properties of the amide derivative (1e) so obtained.

White solid.

Melting point: 23° C.

IR($v_{near}$, cm$^{-1}$): 3425, 2930, 2860, 1650, 1630, 1470, 1380, 1220, 1210, 1120, 720.

$^1$H-NMR(CDCl$_3$, δ): 0.88(br t,J=6.7Hz,6H), 1.17–1.45 (m,49H), 1.45–1.92(m,8H), 2.22–2.45(m,2H), 3.20–3.90(m, 17H), 3.33(s,3H).

Preparation Example 7

An amide derivative (2f) was obtained by conducting a reaction as in step 2 of Preparation Example 1 except that in step 2 of Preparation Example 1, the compound (4e) obtained in step 1 of Preparation Example 6 was used instead of the compound (4a) and methyl hexadecanoate was employed in place of methyl tetradecanoate (steps 1 and 2).

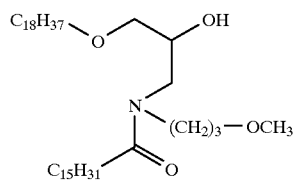
(2f)

The followings are physical properties of the amide derivative (2f) so obtained.

White solid.

Melting point: 54–55° C.

IR($v_{near}$, cm$^{-1}$): 3430, 2930, 2855, 1620, 1470, 1220, 1205, 1110, 950, 885, 720.

$^1$H-NMR(CDCl$_3$, δ): 0.88(br t,J=6.4Hz,6H), 1.25–1.95 (m,61H), 2.36(t,J=7.6Hz,2H), 3.29–3.52(m,10H), 3.33(s, 3H), 3.88–3.95(m,1H).

An amide derivative (3f) was obtained by conducting a reaction as in step 5 of Preparation Example 1 except that in step 5 of Preparation Example 1, the compound (2f) was used instead of the compound (2a) (step 5).

(3f)

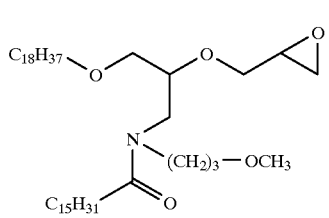

The followings are physical properties of the amide derivative (3f) so obtained.

White solid.

Melting point: 45–47° C.

IR($v_{neat}$, cm$^{-1}$): 2930, 2860, 1650, 1470, 1425, 1380, 1210, 1120, 910, 845, 755, 720.

$^1$H-NMR (CDCl$_3$, δ): 0.88(br t,J=6.7Hz,6H), 1.15–1.45 (m,54H), 1.45–1.73(m,4H), 1.73–1.90(m,2H), 2.25–2.48(m, 2H), 2.50–2.68(m,1H), 2.70–2.85(m,1H), 3.00–3.18(m,1H), 3.18–4.00(m,13H), 3.32(s,3H).

A target amide derivative (1f) was obtained by conducting reactions as in steps 7 and 8 of Preparation Example 1 except that in step 7 of Preparation Example 1, the compound (3f) obtained above (step 5) was used instead of the compound (3a) (steps 7 and 8).

(1f)

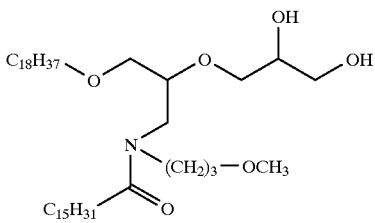

The followings are physical properties of the amide derivative (1f) so obtained.

White solid.

Melting point: 35° C.

IR($v_{neat}$, cm$^{-1}$): 3445, 2930, 2860, 1650, 1630, 1470, 1420, 1380, 1305, 1210, 1120, 1080.

$^1$H-NMR(CDCl$_3$, δ): 0.88(br t,J=6.4Hz,6H), 1.15–1.45 (m,54H), 1.45–1.95(m,7H), 2.25–2.55(m,3H), 3.20–3.95(m, 16H), 3.33(s,3H).

Preparation Example 8

An amino alcohol derivative (4g) was obtained by conducting a reaction as in step 1 of Preparation Example 1 except that in step 1 of Preparation Example 1, tetradecyl glycidyl ether was employed in lieu of hexadecyl glycidyl ether (step 1).

(4g)

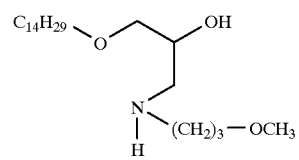

The followings are physical properties of the amino alcohol derivative (4g) so obtained.

White solid.

Melting point: 47° C.

IR($v_{neat}$, cm$^{-1}$): 3340, 2930, 2855, 1470, 1310, 1120, 1065, 995, 900, 720.

$^1$H-NMR(CDCl$_3$, δ): 0.88(t,J=6.3Hz,3H), 1.25–1.45(m, 26H), 1.45–1.85(m,6H), 2.57–2.75(m,4H), 3.32(s,3H), 3.38–3.48(m,6H), 3.75–3.88(m,1H).

An amide derivative (2g) was obtained by conducting a reaction as in step 2 of Preparation Example 1 except that in step 2 of Preparation Example 1, the compound (4g) obtained above (step 1) was used instead of the compound (4a) and methyl hexadecanoate was used in place of methyl tetradecanoate (step 2).

(2g)

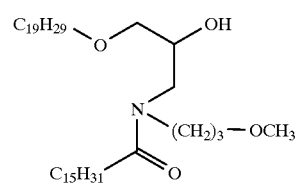

The followings are physical properties of the amide derivative (2g) so obtained.

White solid.

Melting point: 47° C.

IR($v_{neat}$, cm$^{-1}$): 3440, 2930, 2855, 1620, 1470, 1205, 1110, 950, 720.

$^1$H-NMR(CDCl$_3$, δ): 0.88(br t,J=6.4Hz,6H), 1.26–1.89 (m,52H), 2.36(t,J=7.6Hz,2H), 3.29–3.52(m,11H), 3.33(s, 3H), 3.88–3.95(m,1H).

An amide derivative (3g) was obtained by conducting a reaction as in step 5 of Preparation Example 1 except that in step 5 of Preparation Example 1, the compound (2g) obtained above (step 2) was used instead of the compound (2a) (step 5).

(3g)

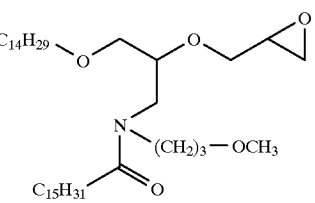

The followings are physical properties of the amide derivative (3g) so obtained.

Colorless clear liquid.

IR($v_{neat}$, cm$^{-1}$) 2930, 2860, 1650, 1470, 1425, 1380, 1210, 1120, 910, 845, 755, 720.

$^{1}$H-NMR(CDCl$_3$, δ): 0.88(br t,J=6.7Hz,6H), 1.15–1.45 (m,46H), 1.45–1.73(m,4H), 1.73–1.90(m,2H), 2.25–2.50(m, 2H), 2.50–2.68(m,1H), 2.70–2.85(m,1H), 3.00–3.18(m,1H), 3.18–4.00(m,13H), 3.32(s,3H).

A target amide derivative (1g) was obtained by conducting reactions as in steps 7 and 8 of Preparation Example 1 except that in step 7 of Preparation Example 1, the compound (3g) obtained above (step 5) was used instead of the compound (3a) (steps 7 and 8).

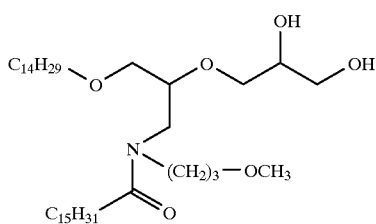

(1g)

The followings are physical properties of the amide derivative (1g) so obtained.

White solid.

Melting point: 27° C.

IR(ν$_{near}$, cm$^{-1}$): 3445, 2930, 2860, 1650, 1630, 1470, 1420, 1380, 1305, 1210, 1120, 1080, 720.

$^{1}$H-NMR(CDCl$_3$, δ): 0.88(br t,J=6.4Hz,6H), 1.15–1.45 (m,45H), 1.45–1.93(m,7H), 2.20–2.60(m,3H), 3.20–3.90(m, 17H), 3.33(s,3H).

Preparation Example 9

An amino alcohol derivative (4h) was obtained by conducting a reaction as in step 1 of Preparation Example 1 except in step 1 of Preparation Example 1, 2-methoxyethylamine was used instead of 3-methoxypropylamine (step 1).

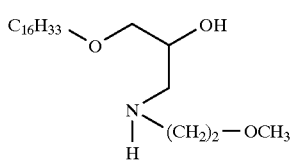

(4h)

The followings are physical properties of the amino alcohol derivative (4h) so obtained.

White solid.

Melting point: 54–55° C.

IR(ν$_{near}$, cm$^{-1}$): 3430, 2920, 2855, 1470, 1120, 1065, 900, 720.

$^{1}$H-NMR(CDCl$_3$, δ): 0.88(t,J=6.3Hz,3H), 1.25–1.70(m, 30H), 2.57–2.76(m,4H), 3.32(s,3H), 3.38–3.48(m,6H), 3.77–3.89(m,1H).

An amide derivative (2h) was obtained by conducting a reaction as in step 2 of Preparation Example 1 except that in step 2 of Preparation Example 1, the compound (4h) obtained above (step 1) was used instead of the compound (4a) and methyl hexadecanoate was used in place of methyl tetradecanoate (step 2).

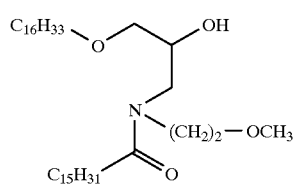

(2h)

The followings are physical properties of the amide derivative (2h) so obtained.

White solid.

Melting point: 51–52° C.

IR(ν$_{near}$, cm$^{-1}$): 3420, 2920, 2855, 1620, 1470, 1110, 720.

$^{1}$H-NMR(CDCl$_3$, δ): 0.87(t,J=6.4Hz,6H), 1.15–1.70(m, 55H), 2.25–2.50(m,2H), 3.20–4.00(m,11H), 3.34(s,3H).

An amide derivative (3h) was obtained by conducting a reaction as in step 5 of Preparation Example 1 except that in step 5 of Preparation Example 1, the compound (2h) obtained above (step 2) was used instead of the compound (2a) (step 5).

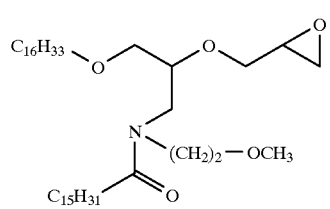

(3h)

The followings are physical properties of the amide derivative (3h) so obtained.

Colorless clear liquid.

IR(ν$_{near}$, cm$^{-1}$): 2930, 2855, 1650, 1470, 1420, 1380, 1310, 1250, 1190, 1120, 910, 850, 720.

$^{1}$H-NMR(CDCl$_3$, δ): 0.88(br t,J=6.4Hz,6H), 1.13–1.45 (m,50H), 1.45–1.70(m,4H), 2.30–2.50(m,2H), 2.50–2.70(m, 1H), 2.70–2.85(m,1H), 3.00–3.20(m,1H), 3.20–4.00(m, 13H), 3.32(s,3H).

A target amide derivative (1h) was obtained by conducting a reaction as in step 6 of Preparation Example 1 except that in step 6 of Preparation Example 1, the compound (3h) obtained above (step 5) was used instead of the compound (3a) (step 6).

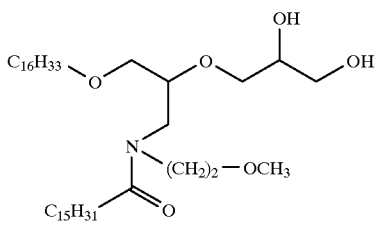

(1h)

The followings are physical properties of the amide derivative (1h) so obtained.

White solid.

Melting point: 31–32° C.

IR($v_{neat}$, cm$^{-1}$): 3450, 2930, 2860, 1630, 1470, 1380, 1300, 1190, 1160, 720.

$^1$H-NMR(CDCl$_3$, δ): 0.88(t,J=6.4Hz,6H), 1.15–1.75(m, 54H), 2.20–2.45(m,3H), 3.20–3.90(m,17H), 3.33(s,3H).

A 1,3-dioxolane-amide derivative (16h) was obtained by conducting a reaction as in step 11 of Preparation Example 3 except that in step 11 of Preparation Example 3, the compound (2h) obtained above (step 2) was used instead of the compound (2b) (step 11).

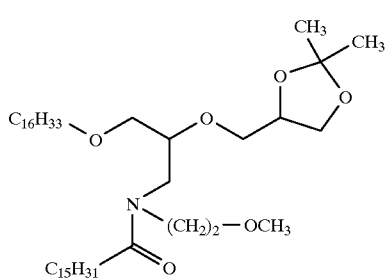

(16h)

The followings are physical properties of the 1,3-dioxolane-amide derivative (16h) so obtained.

Colorless clear liquid.

hu 1H-NMR(CDCl$_3$, δ): 0.88(t,J=6.4Hz,6H), 1.15–1.70 (m,54H), 1.34(s,3H), 1.40(s,3H), 2.36(t,J=7.0Hz,2H), 3.25–4.30(m,19H).

A target amide derivative (1h) was obtained by conducting a reaction as in step 11 of Preparation Example 3 except that in step 10 of Preparation Example 3, the compound (16h) obtained above (step 11) was used instead of the compound (16b) (step 10).

Preparation Example 10

An amino alcohol derivative (4i) was obtained by conducting a reaction as in step 1 of Preparation Example 1 except that in step 1 of Preparation Example 1, ethylamine was used instead of 3-methoxypropylamine (step 1).

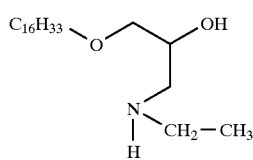

(4i)

The followings are physical properties of the amino alcohol derivative (4i) so obtained.

White solid.

Melting point: 60–61° C.

IR($v_{neat}$, cm$^{-1}$): 3400, 2930, 2855, 1470, 1310, 1110, 955, 720.

$^1$H-NMR(CDCl$_3$, δ): 0.88(t, J=6.4Hz,3H), 1.11(t,J=7.2Hz,3H), 1.15–1.70(m,30H), 2.55–2.80(m,4H), 3.35–3.53 (m,4H), 3.79–3.93(m,1H).

An amide derivative (2i) was obtained by conducting a reaction as in step 2 of Preparation Example 1 except that in step 2 of Preparation Example 1, the compound (4i) obtained above (step 1) was used instead of the compound (4a) and methyl hexadecanoate was used in place of methyl tetradecanoate (step 2).

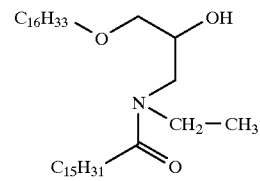

(2i)

The followings are physical properties of the amide derivative (2i) so obtained.

White solid.

Melting point: 56° C.

IR($v_{neat}$, cm$^{-1}$): 3410, 2930, 2860, 1625, 1470, 1380, 1305, 1245, 1210, 1110, 950, 855, 720.

$^1$H-NMR(CDCl$_3$, δ): 0.88(t,J=6.4Hz,6H), 1.15–1.75(m, 57H), 2.34(t,J=7.6Hz,2H), 3.30–3.55(m,9H), 3.85–4.00(m, 1H).

An amide derivative (3i) was obtained by conducting a reaction as in step 5 of Preparation Example 1 except that in step 5 of Preparation Example 1, the compound (2i) obtained above (step 2) was used instead of the compound (2a) (step 5).

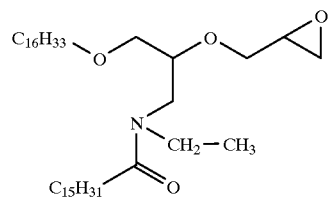

(3i)

The followings are physical properties of the amide derivative (3i) so obtained.

Colorless clear liquid.

IR($v_{neat}$, cm$^{-1}$): 2930, 2855, 1650, 1470, 1425, 1380, 1210, 1120, 905, 840, 720.

$^1$H-NMR(CDCl$_3$, δ): 0.88(br t,J=6.4Hz,6H), 1.10–1.75 (m,57H), 2.25–2.50(m,2H), 2.50–2.70(m,1H), 2.70–2.85(m, 1H), 3.00–4.00(m,12H).

A target amide derivative (1i) was obtained by conducting a reaction as in step 6 of Preparation Example 1 except that in step 6 of Preparation Example 1, the compound (3i) obtained above (step 5) was used instead of the compound (3a) (step 6).

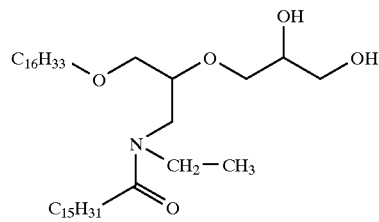

(1i)

The followings are physical properties of the amide derivative (1i) so obtained.

White solid.

Melting point: 35–36° C.

IR($v_{neat}$, cm$^{-1}$): 3445, 2930, 2860, 1630, 1470, 1420, 1380, 1305, 1210, 1120, 720.

$^1$H-NMR(CDCl$_3$, δ): 0.88(br t,J=6.4Hz,6H), 1.13–1.75 (m,57H), 2.31(t,J=7.5Hz,2H), 3.20–3.90(m,16H).

Example 1

Cosmetic compositions were prepared according to Tables 1–5 and appearance, stability and skin-roughness lessening effects were evaluated. The results are shown in Tables 1–5.

Incidentally, the melting point as shown in Tables was measured by charging about 1 mg of a sample in the cell of a differential scanning calorimeter (DSC; 5 μl; product of Seiko Electron Industry) and heating it at the scanning temperature of 100 to 200° C. and a heating rate of 2° C./min. The extrapolation melt starting point according to JIS-K-7121-1987-9-9.1(2) was indicated as the melting point.

(Preparation Process)

The components 1 to 21 were heated and dissolved, followed by the dropwise addition of the components 22 to 29 heated to the same temperature. The reaction mixture was cooled, whereby each cosmetic composition was obtained.

(Evaluation method)

(1) Appearance

The light permeability of each of the cosmetic compositions was measured using a spectrophotometer ("UV-160", product of Shimadzu Corporation). Supposing that the light permeability of distilled water used as a control was designated as 100, the light permeability falling within a range of from 75 to 100 was judged as clear, that not smaller than 20 but less than 75 as semi-clear and that less than 20 as opaque.

(2) Stability

The state of each of the compositions stored at 40° C. and humidity of 75% for one week was visually observed. Compared with the composition immediately after preparation, that showing no change in appearance and properties was judged good, while that showing an apparent change was judged as poor.

(3) Skin roughness lessening effects

Ten female volunteers of ages ranging from 20 to 50 with skin roughness at their cheeks in winter were chosen as subjects. Different cosmetic compositions were coated on the left and right cheeks of each subject for 2 weeks. On the following day after the completion of the coating for 2 weeks, skin conductance was measured. Described specifically, after washing the face with warm water of 37° C., each subject quietly stayed for 20 minutes in a room controlled at a temperature of 20° C. and a humidity of 40%. The water content of her stratum corneum was measured by a skin conductance meter (product of IBS Corp.). A conductance value less than 20 indicates skin roughness so that the effects of the composition were insufficient, while the effects were rated high at a conductance value of at least 20.

TABLE 1

| Component (wt. %) | Invention product | | | | |
| --- | --- | --- | --- | --- | --- |
| | 1 | 2 | 3 | 4 | 5 |
| 1 Polyoxyethylene octyldodecyl ether (20 E.O.) | | | | | |
| 2 Polyoxyethylene hexyldecyl ether (20 E.O.) | | | | | |
| 3 Triisostearic acid polyoxyethylene hydrogenated castor oil (60 E.O.) | | | | | |
| 4 Polyoxyethylene hydrogenated castor oil (60 E.O.) | 2 | 2 | 2 | 2 | 2 |
| 5 Polyoxyethylene sorbitan monostearate (20 E.O.) | | | | | |
| 6 Polyoxyethylene alkyl (C$_{12-15}$) ether sodium phosphate (4 E.O.) | | | | | |
| 7 Amide derivative (1a) (m.p. 25° C.) | 2 | | | | |
| 8 Amide derivative (1b) (m.p. 33° C.) | | 2 | | | |
| 9 Amide derivative (1c) (m.p. 25° C.) | | | 2 | | |
| 10 Amide derivative (1d) (m.p. 32° C.) | | | | 2 | |
| 11 Amide derivative (1e) (m.p. 23° C.) | | | | | 2 |
| 12 Amide derivative (1f) (m.p. 35° C.) | | | | | |
| 13 Amide derivative (1g) (m.p. 27° C.) | | | | | |
| 14 Amide derivative (1h) (m.p. 31° C.) | | | | | |
| 15 Amide derivative (1i) (m.p. 35° C.) | | | | | |
| 16 Natural ceramide (m.p. 105° C.) | | | | | |
| 17 Stearic acid amide (m.p. 100° C.) | | | | | |
| 18 Isotridecyl isononanoate | | | | | |
| 19 Diglyceryl monoisostearate monomyristate | | | | | |

TABLE 1-continued

|  | Invention product | | | | |
|---|---|---|---|---|---|
| Component (wt. %) | 1 | 2 | 3 | 4 | 5 |
| 20 Stearic acid | | | | | |
| 21 Stearyl alcohol | | | | | |
| 22 Citric acid | | | | | |
| 23 Sodium citrate | | | | | |
| 24 Succinic acid | | | | | |
| 25 Sodium monohydrogenphosphate | | | | | |
| 26 86% glycerin | | | | | |
| 27 1,3-Butylene glycol | | | | | |
| 28 Ethanol | | | | | |
| 29 Water | Balance | Balance | Balance | Balance | Balance |
| Properties | Toilet water | Toilet water | Toilet water | Toilet water | Toilet water |
| Appearance | Clear | Clear | Clear | Clear | Clear |
| Stability | Good | Good | Good | Good | Good |
| Skin roughness lessening effects | High | High | High | High | High |

TABLE 2

|  | Invention product | | | | |
|---|---|---|---|---|---|
| Component (wt. %) | 6 | 7 | 8 | 9 | 10 |
| 1 Polyoxyethylene octyldodecyl ether (20 E.O.) | | | | | |
| 2 Polyoxyethytene hexyldecyl ether (20 E.O.) | | | | | |
| 3 Triisostearic acid polyoxyethylene hydrogenated castor oil (60 E.O.) | | | | | |
| 4 Polyoxyethylene hydrogenated castor oil (60 E.O.) | 2 | 2 | 2 | 2 | |
| 5 Polyoxyethylene sorbitan monostearate (20 E.O.) | | | | | 1 |
| 6 Polyoxyethylene alkyl ($C_{12-18}$) ether phosphate (4 E.O.) | | | | | 1 |
| 7 Amide derivative (1a) (m.p. 25° C.) | | | | | 5 |
| 8 Amide derivative (1b) (m.p. 33° C.) | | | | | |
| 9 Amide derivative (1c) (m.p. 25° C.) | | | | | |
| 10 Amide derivative (1d) (m.p. 32° C.) | | | | | |
| 11 Amide derivative (1e) (m.p. 23° C.) | | | | | |
| 12 Amide derivative (1f) (m.p. 35° C.) | 2 | | | | |
| 13 Amide derivative (1g) (m.p. 27° C.) | | 2 | | | |
| 14 Amide derivative (1h) (m.p. 31° C.) | | | 2 | | |
| 15 Amide derivative (1i) (m.p. 35° C.) | | | | 2 | |
| 16 Natural ceramide (m.p. 105° C.) | | | | | |
| 17 Stearic acid amide (m.p. 100° C.) | | | | | |
| 18 Isotridecyl isononanoate | | | | | |
| 19 Diglyceryl monoisostearate monomyristate | | | | | |
| 20 Stearic acid | | | | | |
| 21 Stearyl alcohol | | | | | |
| 22 Citric acid | | | | | |
| 23 Sodium citrate | | | | | |
| 24 Succinic acid | | | | | |
| 25 Sodium monohydrogenphosphate | | | | | |
| 26 86% glycerin | | | | | |
| 27 1,3-Butylene glycol | | | | | |
| 28 Ethanol | | | | | |

TABLE 2-continued

|  | Invention product | | | | |
| --- | --- | --- | --- | --- | --- |
| Component (wt. %) | 6 | 7 | 8 | 9 | 10 |
| 29 Water | Balance | Balance | Balance | Balance | Balance |
| Properties | Toilet water | Toilet water | Toilet water | Toilet water | Toilet water |
| Appearance | Clear | Clear | Clear | Clear | Clear |
| Stability | Good | Good | Good | Good | Good |
| Skin roughness lessening effects | High | High | High | High | High |

TABLE 3

|  | Invention product | | | | |
| --- | --- | --- | --- | --- | --- |
| Component (wt. %) | 11 | 12 | 13 | 14 | 15 |
| 1 Polyoxyethylene octyldodecyl ether (20 E.O.) |  |  |  |  | 5 |
| 2 Polyoxyethylene hexyldecyl ether (20 E.O.) |  |  |  | 2 |  |
| 3 Triisostearic acid polyoxyethylene hydrogenated castor oil (60 E.O.) |  | 3 |  |  |  |
| 4 Polyoxyethylene hydrogenated castor oil (60 E.O.) | 3 |  | 3 |  |  |
| 5 Polyoxyethylene sorbitan monostearate (20 E.O.) |  |  |  |  |  |
| 6 Sodium polyoxyethylene alkyl ($C_{12-18}$)phosphate (4 E.O.) |  |  |  |  |  |
| 7 Amide derivative (1a) (m.p. 25° C.) |  |  |  |  |  |
| 8 Amide derivative (1b) (m.p. 33° C.) | 5 |  |  |  |  |
| 9 Amide derivative (1c) (m.p. 25° C.) |  | 5 |  |  |  |
| 10 Amide derivative (1d) (m.p. 32° C.) |  |  | 3 |  |  |
| 11 Amide derivative (1e) (m.p. 23° C.) |  |  |  | 2 |  |
| 12 Amide derivarive (1f) (m.p. 35° C.) |  |  |  |  | 5 |
| 13 Amide derivative (1g) (m.p. 27° C.) |  |  |  |  |  |
| 14 Amide derivative (1h) (m.p. 31° C.) |  |  |  |  |  |
| 15 Amide derivative (1i) (m.p. 35° C.) |  |  |  |  |  |
| 16 Natural ceramide (m.p. 105° C.) |  |  |  |  |  |
| 17 Stearic acid amide (m.p. 100° C.) |  |  |  |  |  |
| 18 Isotridecyl isononanoate | 1 |  | 1 |  | 5 |
| 19 Diglyceryl monoisostearate monomyristate |  | 1 |  |  |  |
| 20 Stearic acid |  |  |  |  | 2 |
| 21 Stearyl alcohol |  |  |  |  | 2 |
| 22 Citric acid |  |  | 0.5 |  | 0.2 |
| 23 Sodium citrate |  |  | 0.5 |  | 0.2 |
| 24 Succinic acid |  |  |  | 0.5 | 0.2 |
| 25 Sodium monohydrogenphosphate |  |  |  | 1 | 0.5 |
| 26 86% glycerin |  |  | 10 | 20 | 10 |
| 27 1,3-Butylene glycoi |  |  | 5 | 2 | 3 |
| 28 Ethanol |  |  | 5 | 2 | 3 |
| 29 Water | Balance | Balance | Balance | Balance | Balance |
| Properties | Toilet water | Toilet water | Toilet water | Toilet water | Cream |
| Appearance | Semi-Clear | Semi-Clear | Semi-Clear | Semi-Clear | Opaque |
| Stability | Good | Good | Good | Good | Good |
| Skin roughness lessening effects | High | High | High | High | High |

TABLE 4

| Component (wt. %) | Invention product 16 | Comparative product 1 | Comparative product 2 | Comparative product 3 | Comparative product 4 |
|---|---|---|---|---|---|
| 1 Polyoxyethylene octyldodecyl ether (20 E.O.) | | | | | 5 |
| 2 Polyoxyethylene hexyldecyl ether (20 E.O.) | | | | | |
| 3 Triisostearic acid polyoxyethylene hydrogenated castor oil (60 E.O.) | | | 3 | | |
| 4 Polyoxyethylene hydrogenated castor oil (60 E.O.) | | 2 | | 3 | |
| 5 Polyoxyethylene sorbitan monostearate (20 E.O.) | 1 | | | | |
| 6 Polyoxyethylene alkyl ($C_{12-18}$) ether phosphate (4 E.O.) | | | | | |
| 7 Amide derivative (1a) (m.p. 25° C.) | 1 | | | | |
| 8 Amide derivative (1b) (m.p. 33° C.) | | | | | |
| 9 Amide derivative (1c) (m.p. 25° C.) | | | | | |
| 10 Amide derivative (1d) (m.p. 32° C.) | | | | | |
| 11 Amide derivative (1e) (m.p. 23° C.) | | | | | |
| 12 Amide derivative (1f) (m.p. 35° C.) | | | | | |
| 13 Amide derivative (1g) (m.p. 27° C.) | | | | | |
| 14 Amide derivative (1h) (m.p. 31° C.) | | | | | |
| 15 Amide derivative (1i) (m.p. 35° C.) | | | | | |
| 16 Natural ceramide (m.p. 105° C.) | | 2 | 5 | | 5 |
| 17 Stearic acid amide (m.p. 100° C.) | | | | 3 | |
| 18 Isotridecyl isononanoate | | | | 1 | 5 |
| 19 Diglyceryl monoisostearate monomyristate | 2 | | 1 | | |
| 20 Stearic acid | 0.5 | | | | 2 |
| 21 Stearyl alcohol | 0.5 | | | | 2 |
| 22 Citric acid | 0.1 | | | 0.5 | 0.2 |
| 23 Sodium citrate | 0.1 | | | 0.5 | 0.2 |
| 24 Succinic acid | 0.1 | | | | 0.2 |
| 25 Sodium monohydrogenphosphate | 0.1 | | | | 0.5 |
| 26 86% glycerin | 5 | | | 10 | 10 |
| 27 1,3-Butylene glycol | 1 | | | 5 | 3 |
| 28 Ethanol | 1 | | | 5 | 3 |
| 29 Water | Balance | Balance | Balance | Balance | Balance |
| Properties | Milky lotion | Toilet water | Toilet water | Toilet water | Cream |
| Appearance | Opaque | Opaque | Opaque | Opaque | Opaque |
| Stability | Good | Poor | Poor | Poor | Poor |
| Skin roughness lessening effects | High | Low | Low | Low | Low |

TABLE 5

| Component (wt. %) | Comparative product 5 | Comparative product 6 |
|---|---|---|
| 1 Polyoxyethylene octyldodecyl ether (20E.O.) | | |
| 2 Polyoxyethylene hexyldecyl ether (20E.O.) | | |
| 3 Triisostearic acid polyoxyethylene hydrogenated castor oil (60E.O.) | | |
| 4 Polyoxyethylene hydrogenated castor oil (60E.O.) | | |
| 5 Polyoxyethylene sorbitan monostearate (20E.O.) | 1 | |
| 6 Polyoxyethylene alkyl ($C_{12-18}$) ether phosphate (4E.O.) | | |
| 7 Amide derivative (1a) (m.p. 25° C.) | | 5 |
| 8 Amide derivative (1b) | | |

TABLE 5-continued

| | | Comparative product | |
|---|---|---|---|
| | Component (wt. %) | 5 | 6 |
| | (m.p. 33° C.) | | |
| 9 | Amide derivative (1b) (m.p. 25° C.) | | |
| 10 | Amide derivative (1c) (m.p. 32° C.) | | |
| 11 | Amide derivative (1e) (m.p. 23° C.) | | |
| 12 | Amide derivative (1f) (m.p. 35° C.) | | |
| 13 | Amide derivative (1g) (m.p. 27° C.) | | |
| 14 | Amide derivative (1h) (m.p. 31° C.) | | |
| 15 | Amide derivative (1i) (m.p. 35° C.) | | |
| 16 | Natural ceramide (m.p. 105° C.) | | |
| 17 | Stearic acid amide (m.p. 100° C.) | 1 | |
| 18 | Isotridecyl isononanoate | | |
| 19 | Diglyceryl monoisostearate monomyristate | 2 | |
| 20 | Stearic acid | 0.5 | |
| 21 | Stearyl alcohol | 0.5 | |
| 22 | Citric acid | 0.1 | |
| 23 | Sodium citrate | 0.1 | |
| 24 | Succinic acid | 0.1 | |
| 25 | Sodium monohydrogen - phosphate | 0.1 | |
| 26 | 86% glycerin | 5 | |
| 27 | 1,3-Butylene glycol | 1 | |
| 28 | Ethanol | 1 | |
| 29 | Water | Balance | Balance |
| | Properties | Milky lotion | Separated |
| | Appearance | Opaque | Opaque |
| | Stability | Poor | Poor |
| | Skin roughness lessening effects | Low | Low |

As is apparent from the results shown in Tables 1–5, each of the cosmetic compositions according to the present invention had excellent stability and high skin-roughness lessening effects.

What is claimed is:

1. A cosmetic composition comprising the following components (A) and (B):

(A) an amide compound having a melting point of 0 to 50° C., and (B) a hydrophilic surfactant, wherein the weight ratio of the component (A) to (B) falls within a range of from 1:0.01 to 1:10, wherein the component (A) is an N-substituted amide compound having at least 30 carbon atoms in total, and wherein the component (A) is selected from the group consisting of amide derivatives represented by the following formulas (1) to (3):

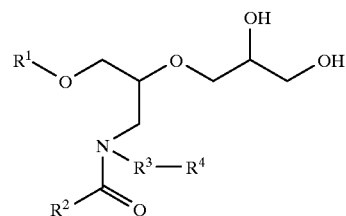

(1)

wherein $R^1$ and $R^2$ are the same or different and each independently represents a $C_{1-40}$ hydrocarbon group which may be hydroxylated, $R^3$ represents a linear or branched $C_{1-6}$ alkylene group or a single bond, and $R^4$ represents a hydrogen atom, a linear or branched $C_{1-12}$ alkoxy group or a 2,3- dihydroxypropyloxy group, with the proviso that when $R^3$ represents a single bond, $R^4$ is a hydrogen atom,

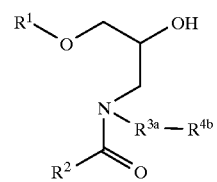

(2)

wherein $R^1$ and $R^2$ have the same meanings as defined above, $R^{3a}$ represents a linear or branched $C_{3-6}$ alkylene group, and $R^{4a}$ represents a linear or branched $C_{1-12}$ alkoxy group,

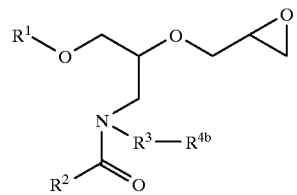

(3)

wherein $R^1$, $R^2$ and $R^3$ have the same meanings as defined above, and $R^{4b}$ represents a hydrogen atom, a linear or branched $C_{1-12}$ alkoxy group or a 2,3- epoxypropyloxy group, with the proviso that when $R^3$ represents a single bond, $R^{4b}$ is a hydrogen atom.

2. A cosmetic composition according to claim 1, which comprises the component (A) in an amount of 0.02 to 20 wt. %.

3. A cosmetic composition according to claim 1, wherein the component (B) comprises at least one surfactant selected from the group consisting of nonionic surfactants, anionic surfactants, amphoteric surfactants and cationic surfactants having an HLB of 8 to 20.

4. A cosmetic composition according to claim 1, which comprises the component (A) in an amount of 0.02 to 20 wt. %, the component (B) in an amount of 0.002 to 10 wt. % and water in an amount of 70 to 99.9 wt. %.

5. A cosmetic composition according to claim 1, which has clear or semi-clear appearance.

* * * * *